(12) United States Patent
Brody et al.

(10) Patent No.: US 11,857,602 B2
(45) Date of Patent: *Jan. 2, 2024

(54) GROWTH HORMONE ANTAGONIST AND ANTI-CANCER COMPOSITION COMBINATION THERAPY

(71) Applicants: Molecular Technologies Laboratories LLC, Galena, OH (US); Ohio University, Athens, OH (US)

(72) Inventors: Richard S. Brody, Columbus, OH (US); Thomas J. Zupancic, Powel, OH (US); Uday Sandbhor, Hilliard, OH (US); John J. Kopchick, Athens, OH (US); Reetobrata Basu, Athens, OH (US)

( * ) Notice: Subject to any disclaimer, the term of this patent is extended or adjusted under 35 U.S.C. 154(b) by 143 days.

This patent is subject to a terminal disclaimer.

(21) Appl. No.: 17/411,497

(22) Filed: Aug. 25, 2021

(65) Prior Publication Data

US 2022/0040266 A1    Feb. 10, 2022

Related U.S. Application Data

(63) Continuation-in-part of application No. 16/903,644, filed on Jun. 17, 2020, now Pat. No. 11,452,763.

(60) Provisional application No. 62/862,222, filed on Jun. 17, 2019.

(51) Int. Cl.
| | |
|---|---|
| *A61K 38/27* | (2006.01) |
| *A61K 45/06* | (2006.01) |
| *A61K 47/10* | (2017.01) |
| *A61K 47/60* | (2017.01) |
| *A61P 35/00* | (2006.01) |
| *A61K 39/00* | (2006.01) |

(52) U.S. Cl.
CPC .............. *A61K 38/27* (2013.01); *A61K 45/06* (2013.01); *A61K 47/10* (2013.01); *A61P 35/00* (2018.01); *A61K 2039/505* (2013.01)

(58) Field of Classification Search
CPC ........ A61K 38/27; A61K 45/06; A61K 47/10; A61K 47/60; A61P 35/00
See application file for complete search history.

(56) References Cited

U.S. PATENT DOCUMENTS

| | | | | |
|---|---|---|---|---|
| 7,399,839 B2 * | 7/2008 | Cox | ........................ | C07K 14/72 |
| | | | | 530/402 |
| 8,778,880 B2 * | 7/2014 | Cho | ........................ | A61P 37/02 |
| | | | | 514/11.3 |
| 10,874,717 B2 * | 12/2020 | Brody | .................... | A61K 47/60 |

OTHER PUBLICATIONS

Muller et al., "Growth Hormone Receptor Antagonists," The Journal of Clinical Endocrinology & Metabolism, 2004, 89(4): 1503-1511. (Year: 2004).*
SOMAVERT from RxList. pp. 1-43. Accessed on Jan. 20, 2022. (Year: 2022).*

* cited by examiner

*Primary Examiner* — Julie Ha

(57) ABSTRACT

A composition for treating a disease or condition responsive to human growth hormone receptor antagonists, comprising a modified human growth hormone receptor antagonist; and an anti-cancer composition. A method for treating cancer using human growth hormone antagonists, comprising pre-screening a patient by analyzing a tumor biopsy to confirm the presence of cancer and the presence of certain predetermined factors indicative of responsiveness to human growth hormone antagonists; and treating the patient with an effective amount of a composition that includes a modified human growth hormone receptor antagonist and an anti-cancer composition.

8 Claims, 19 Drawing Sheets

Specification includes a Sequence Listing.

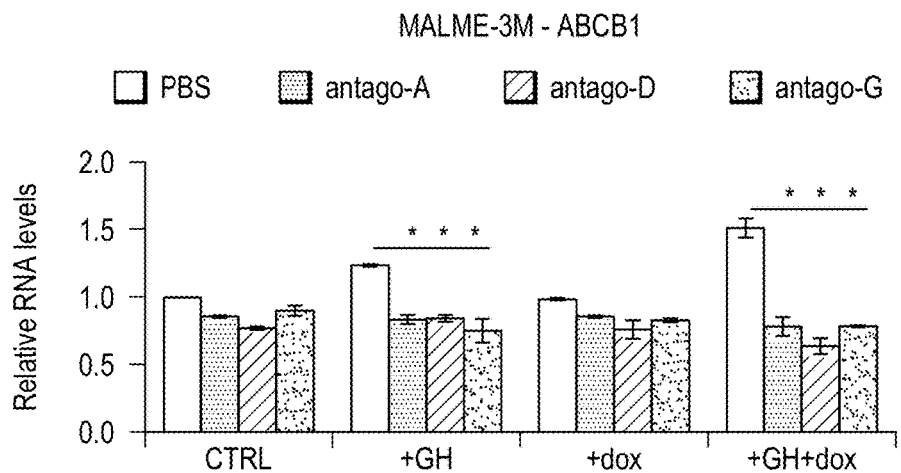
FIG. 5A(1)
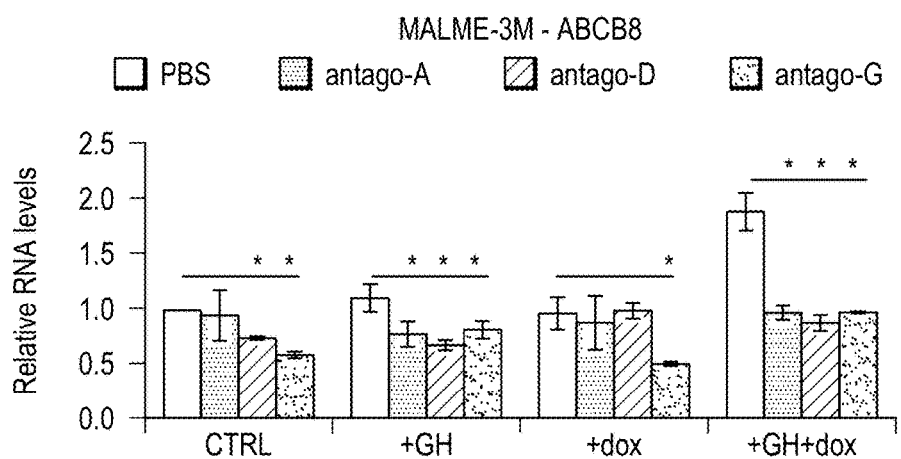
FIG. 5A(2)
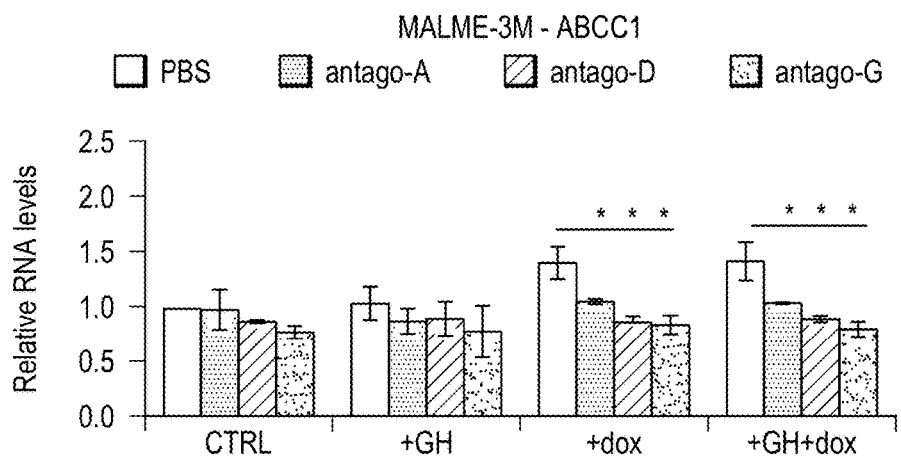
FIG. 5A(3)

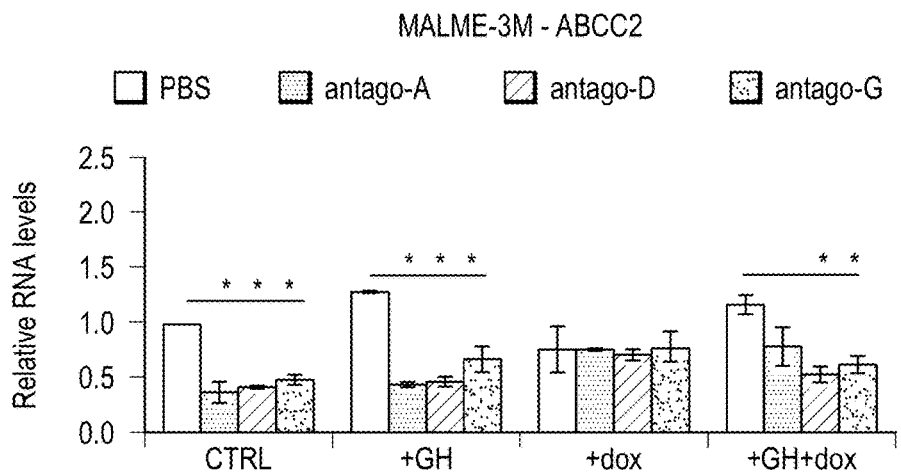
FIG. 5A(4)
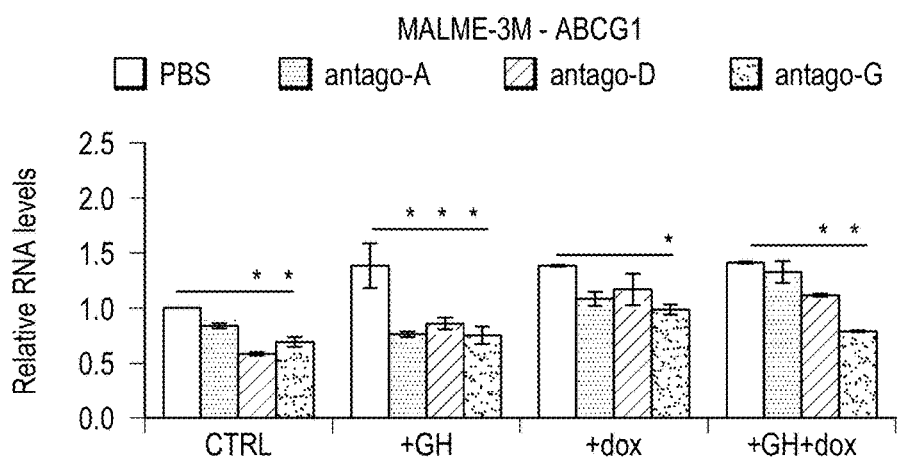
FIG. 5A(5)
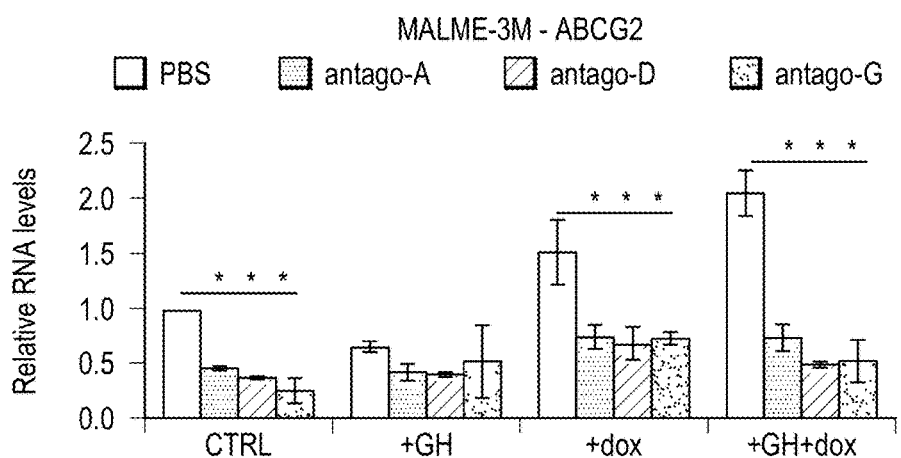
FIG. 5A(6)

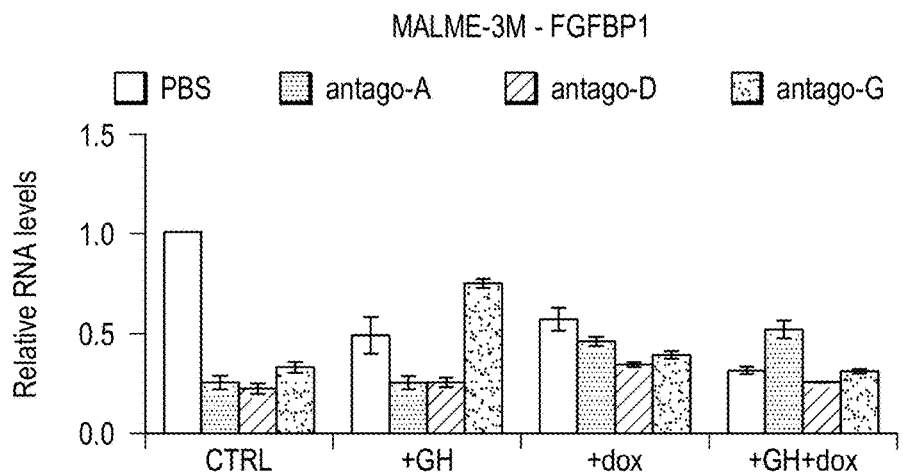
FIG. 5B(1)
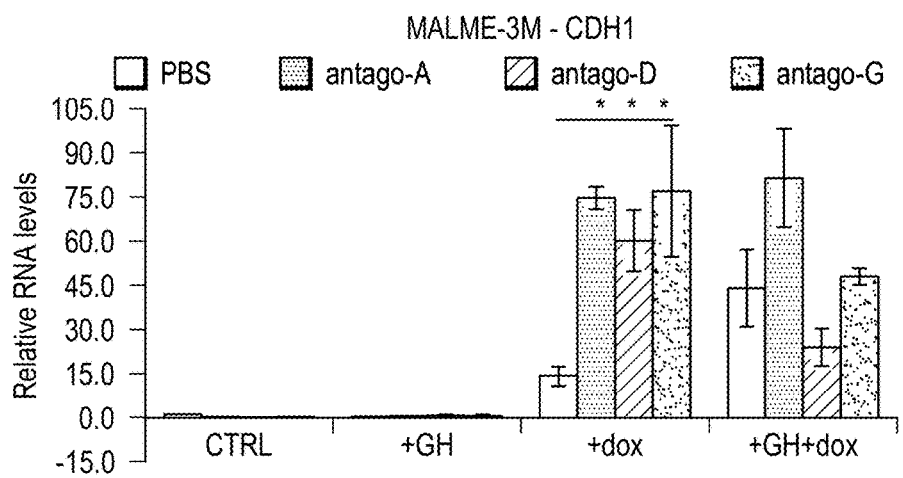
FIG. 5B(2)
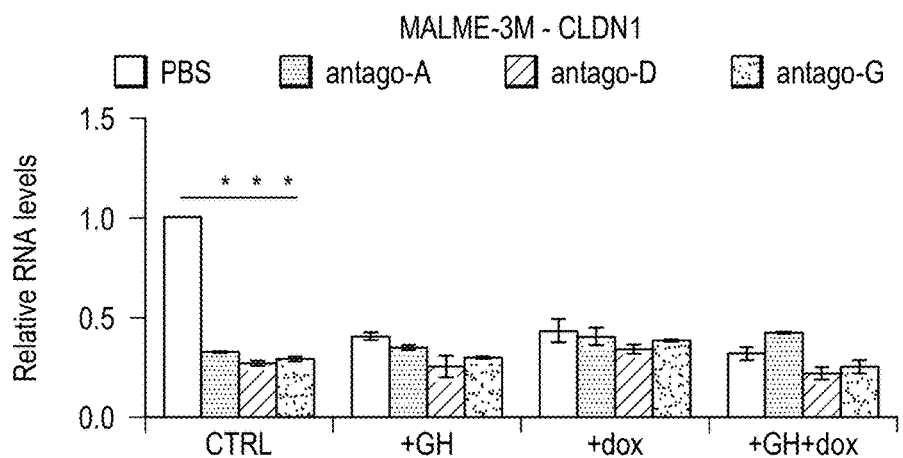
FIG. 5B(3)

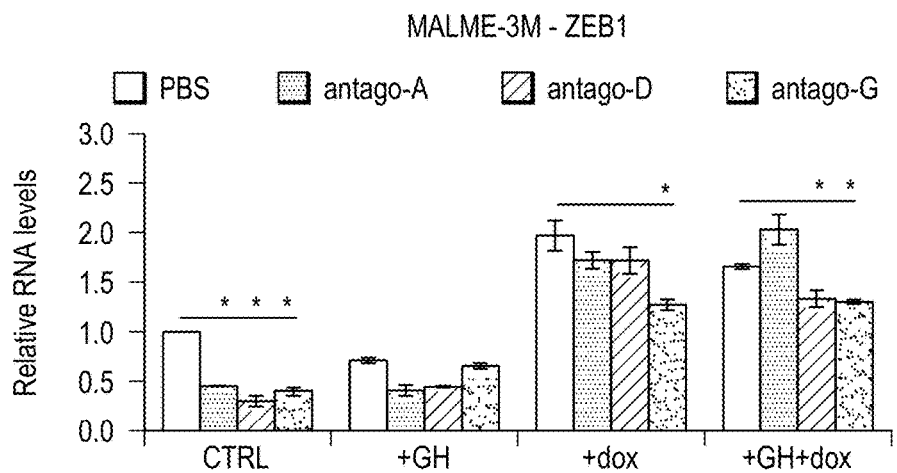
FIG. 5B(4)
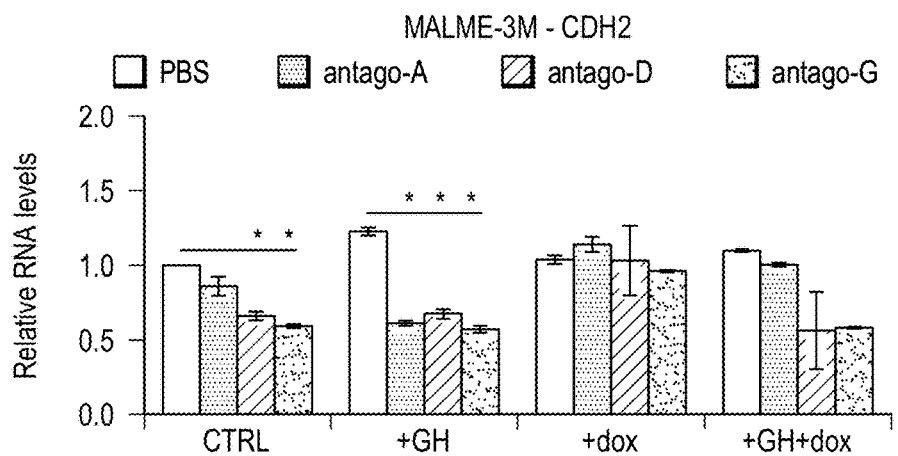
FIG. 5B(5)
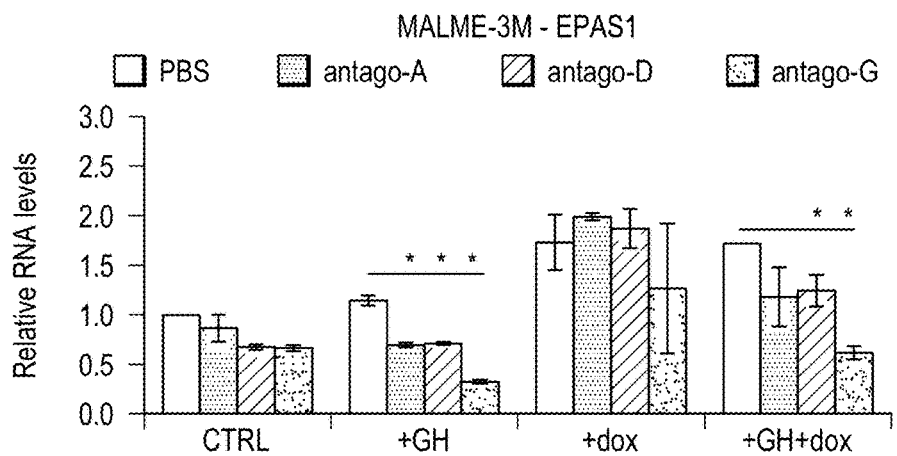
FIG. 5B(6)

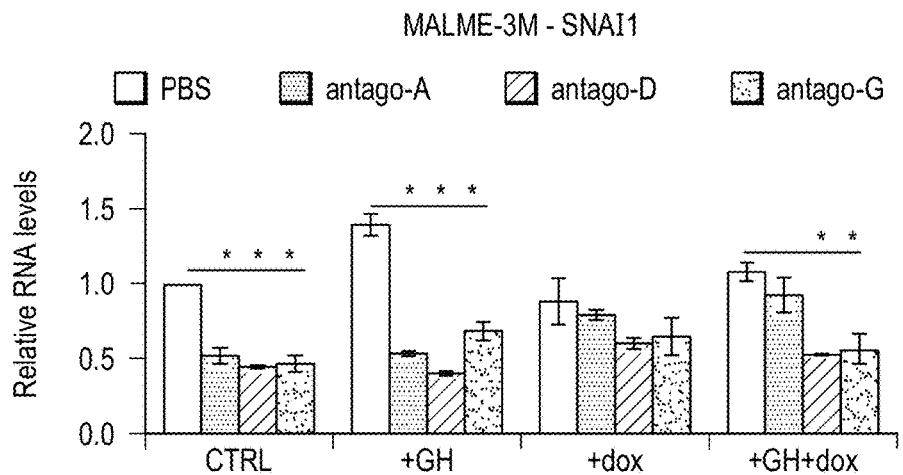
FIG. 5B(7)
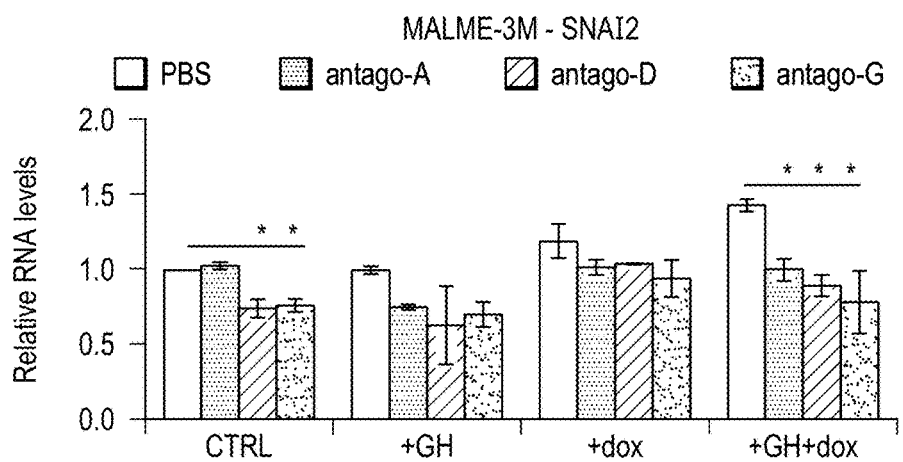
FIG. 5B(8)
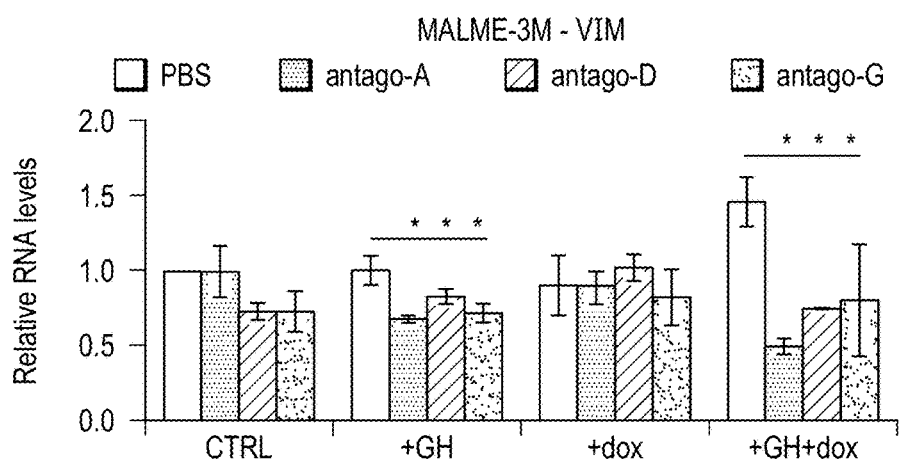
FIG. 5B(9)

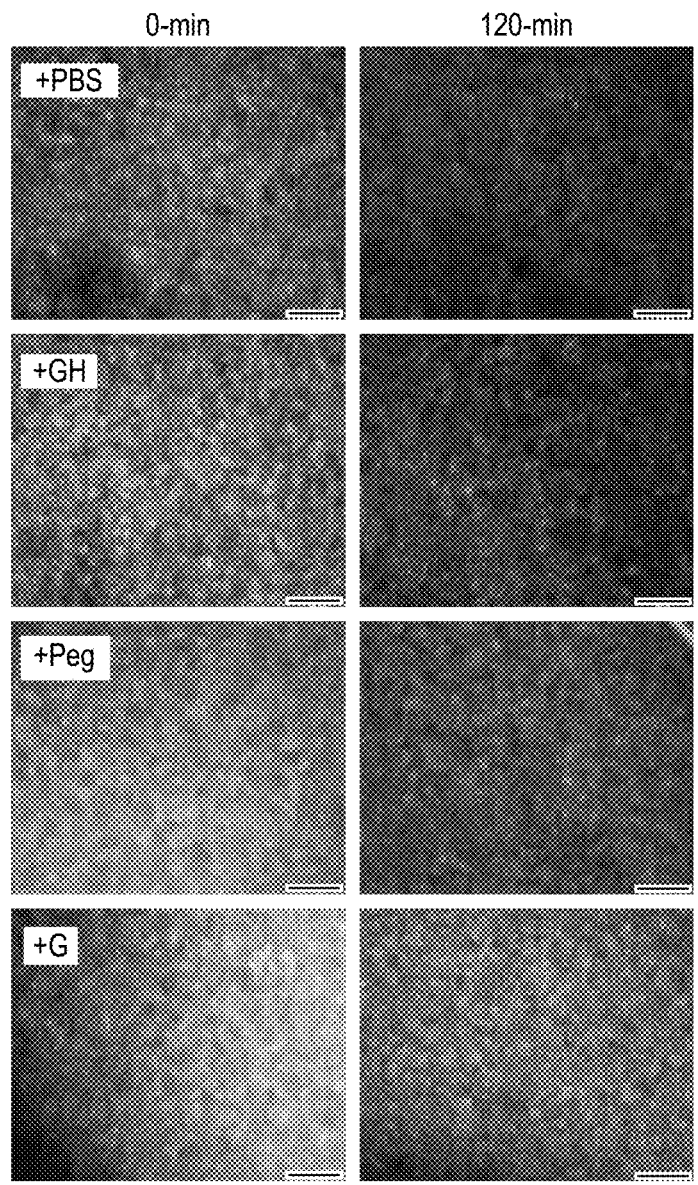
FIG. 7C(1) FIG. 7C(2)
FIG. 7C(3) FIG. 7C(4)
FIG. 7C(5) FIG. 7C(6)
FIG. 7C(7) FIG. 7C(8)

GROWTH HORMONE ANTAGONIST AND ANTI-CANCER COMPOSITION COMBINATION THERAPY

CROSS-REFERENCE TO RELATED APPLICATIONS

This patent application is a continuation-in-part of U.S. patent application Ser. No. 16/903,644 filed on Jun. 17, 2020 and entitled "Therapeutic Pegylated Growth Hormone Antagonists", the disclosure of which is hereby incorporated by reference herein in its entirety and made part of the present U.S. utility patent application for all purposes.

REFERENCE TO A SEQUENCE LISTING

A sequence listing in computer readable form (CRF) is on file. The sequence listing is in an ASCII text (.txt) file entitled SEQIDNOS_1_4 ST25_CIP1.txt created on Aug. 20, 2021, and is 6 KB in size. The sequence listing is incorporated by reference as if fully recited herein.

BACKGROUND

The disclosed inventive technology relates in general to compositions and methods for treating cancer and other diseases, and more specifically to a combination therapy for treating cancer that includes a growth hormone antagonist combined with at least one anti-cancer composition, substance, or drug, wherein the combination therapy prevents the development of drug resistance.

Human growth hormone (hGH or GH), also known as somatotropin or somatropin, is a peptide hormone that stimulates growth, cell reproduction, and regeneration in humans and other animals. Growth hormone is a type of mitogen that is specific only to certain kinds of cells and is a 191-amino acid, single-chain polypeptide that is synthesized, stored, and secreted by somatotropic cells within the lateral wings of the anterior pituitary gland. Acromegaly is a syndrome that results when the anterior pituitary gland produces excess GH after epiphyseal plate closure at puberty. If GH is produced in excess prior to epiphyseal plate closure, the result is gigantism (or giantism). A number of disorders may increase pituitary GH output, although most commonly it involves a tumor called pituitary adenoma, derived from a distinct type of cell (somatotrophs). Acromegaly most commonly affects adults in middle age and can result in severe disfigurement, complicating conditions, and premature death if untreated. Because of its pathogenesis and slow progression, the disease is hard to diagnose in the early stages and is frequently missed for years until changes in external features, especially of the face, become noticeable.

A receptor is a protein molecule usually found embedded within the plasma membrane surface of a cell that receives chemical signals from outside the cell. When such chemical signals bind to a receptor these signals cause some form of cellular/tissue response such as, for example, a change in the electrical activity of the cell. In this sense, a receptor is a protein molecule that recognizes and responds to endogenous chemical signals. An agonist, such as human growth hormone, is a chemical composition that binds to a receptor and activates the receptor to produce a biological response. Whereas an agonist causes an action, an antagonist blocks the action of the agonist, and an inverse agonist causes an action opposite to that of the agonist. A receptor antagonist is a type of receptor ligand or drug that blocks or dampens agonist-mediated responses rather than provoking a biological response itself upon binding to a receptor. These compositions are sometimes called blockers and examples include alpha blockers, beta blockers, and calcium channel blockers. In pharmacology, antagonists have affinity but no efficacy for their cognate receptors, and binding will disrupt the interaction and inhibit the function of an agonist or inverse agonist at receptors. Antagonists mediate their effects by binding to the active (orthosteric) site or to other (allosteric) sites on receptors, or they may interact at unique binding sites not normally involved in the biological regulation of the receptor's activity. Antagonist activity may be reversible or irreversible depending on the longevity of the antagonist—receptor complex, which, in turn, depends on the nature of antagonist—receptor binding. Most drug antagonists achieve their potency by competing with endogenous ligands or substrates at structurally defined binding sites on receptors. By definition, antagonists display no efficacy to activate the receptors they bind, and antagonists do not maintain the ability to activate a receptor. Once bound, however, antagonists inhibit the function of agonists, inverse agonists, and partial agonists.

Growth hormone receptor antagonists such as the product SOMAVERT® (pegvisomant) are used in the treatment of acromegaly. Such compositions are used if the tumor of the pituitary gland causing the acromegaly cannot be controlled with surgery or radiation and the use of somatostatin analogues is unsuccessful. SOMAVERT® (pegvisomant) is typically delivered as a powder that is mixed with water and injected under the skin.

Pegylation is the process of both covalent and non-covalent amalgamation of polyethylene glycol (PEG) polymer chains to molecules and macrostructures, such as drugs, peptides, antibody fragments, or therapeutic proteins. Pegylation is routinely achieved by incubation of a reactive derivative of PEG with the target molecule and produces alterations in physiochemical properties, including changes in molecular size and molecular charge. These physical and chemical changes increase systemic retention of the therapeutic agent and can influence the binding affinity of the therapeutic moiety to the cell receptors and can alter the absorption and distribution patterns. The covalent attachment of PEG to a drug or therapeutic protein can also "mask" the agent from the host's immune system (i.e., reducing immunogenicity and antigenicity), and increase the hydrodynamic size (i.e., size in solution) of the agent which prolongs its circulatory time by reducing renal clearance. Pegylation can also provide water solubility to hydrophobic drugs and proteins.

Pegylation, by increasing the molecular weight of a molecule, can impart several significant pharmacological advantages over the unmodified form of the molecule, such as: (i) improved drug solubility; (ii) reduced dosage frequency, without diminished efficacy and with potentially reduced toxicity; (iii) extended circulating life; (iv) increased drug stability; and (v) enhanced protection from proteolytic degradation. PEGylated drugs also include the following commercial advantages: (i) opportunities for new delivery formats and dosing regimens; and (ii) extended patent life of previously approved drugs. PEG is a particularly attractive polymer for conjugation and the specific characteristics of PEG moieties relevant to pharmaceutical applications include: (i) water solubility; (ii) high mobility in solution; (iii) lack of toxicity and low immunogenicity; and (iv) altered distribution in the body.

The addition of high molecular weight polyethylene glycols (PEGs) to proteins has been previously shown to increase the in-vivo half-lives of these proteins by a size dependent decrease in elimination by the kidneys. The addition of PEGs also lowers the immunogenicity of the proteins and decreases aggregation and protease cleavage [1]-[2]. Multiple known PEGylated proteins have been approved by the USFDA for therapeutic use, including hormones, cytokines, antibody fragments, and enzymes [1] and [3]-[4]. Thus, there is an ongoing need for the further development of PEGylated therapeutics, particularly for use in the treatment of diseases that are responsive to the use of GH receptor antagonists or other receptor antagonists.

Evidence from human studies [5], animal studies [6], and cancer cell line studies [6] supports a role for growth hormone (GH) in carcinogenesis. The relationship between GH receptor (GHR) expression and function in the following human cancers has been reviewed; breast cancer, liver cancer, prostate cancer, colon cancer, melanoma, pancreatic cancer, endometrial cancer, meningioma, neuroblastoma, glioma, lung cancer, and stomach cancer [6]. Both in vitro studies with cancer cell lines and in vivo studies with human tumor xenografts in nude mice indicate that attenuating GH action has anti-cancer effects. The effects of GH on cancer have been shown to be inhibited either by reducing the expression of the GH receptor (GHR) or by use of the GHR antagonist, SOMAVERT® (pegvisomant) [6]. There is also in vivo and in vitro evidence that, for breast and prostate cancers, attenuating prolactin (PRL) action has, in many cases, anti-cancer effects [7].

The use of GHR antagonists in cancer therapy is contingent on the cancer cells expressing the GHR or the prolactin receptor (PRLR) or both the GHR and PRLR. The level of GHR expression and the level of PRLR expression has been determined in 60 cancer cell lines from nine types of human cancer: breast, CNS, colon, leukemia, melanoma, non-small cell lung, ovarian, prostate, and renal [8]. High GHR expression levels were obtained with most of the cell lines for all the cancer types except for colon cancer and leukemia. High PRLR expression levels were obtained for most of the cell lines with all the cancer types except for leukemia and prostate cancer.

Chemotherapy is the most common form of cancer treatment, but in many cases cancers develop resistance to chemotherapy over time [9]. This drug resistance is a major cause of cancer deaths. The effects of GH on the development of chemotherapy resistance have recently been reviewed [10]. Studies have used GH, GHR knockout mice (GHRKO), and the hGHR antagonist, SOMAVERT' (pegvisomant) to investigate the effects of GH/GHR signaling on cancer drug resistance [10]. In vitro, studies with cancer cell lines indicate that GH promotes cancer drug resistance by protecting cells from apoptosis, stimulating the epithelial to mesenchymal transition (EMT), stimulating the expression of ATP-binding cassette (ABC) transporters (drug efflux pumps), and promotion of cancer stem cells. There is also evidence that PRL promotes cancer drug resistance by way of upregulating ABC transporters and promoting cancer stem-like properties [12].

SOMAVERT® (pegvisomant) has been shown to reverse the GH stimulated resistance of breast cancer cells in vitro to the drug doxorubicin in cell proliferation studies [13]. SOMAVERT® (pegvisomant) has also been shown to reverse GH promoted resistance to doxorubicin induced apoptosis in a cell culture assays. A novel GHR antagonist (referred to herein as "Compound G") has been prepared that binds to the GHR more tightly than SOMAVERT® (pegvisomant) (see U.S. Pat. No. 10,874,717, which is incorporated by reference herein in its entirety). Unlike SOMAVERT® (pegvisomant), Compound G also binds tightly to the PRLR (see U.S. patent application Ser. No. 16/903,644, which is incorporated by reference herein in its entirety). The ability of Compound G to reverse GH stimulated drug resistance both in vitro and in vivo is described herein.

SUMMARY

The following provides a summary of certain example implementations of the disclosed inventive subject matter. This summary is not an extensive overview and is not intended to identify key or critical aspects or elements of the disclosed inventive subject matter or to delineate its scope. However, it is to be understood that the use of indefinite articles in the language used to describe and claim the disclosed inventive subject matter is not intended in any way to limit the described inventive subject matter. Rather the use of "a" or "an" should be interpreted to mean "at least one" or "one or more".

One implementation of the disclosed technology provides a composition and method for treating a disease or condition responsive to human growth hormone receptor antagonists. The composition comprises a modified human growth hormone receptor antagonist, and an anti-cancer composition. The method for treating diseases or conditions responsive to human growth hormone receptor antagonists, comprises administering to a patient an effective amount of the composition. The disease or condition responsive to human growth hormone receptor antagonists may be a cancer that expresses predetermined levels of growth hormone receptor (GHR); predetermined levels of prolactin receptor (PRLR); predetermined levels of both GHR and PRLR); predetermined levels of ATP-binding cassette (ABC)-transporters; or predetermined levels of epithelial to mesenchymal transition (EMT) mediators. The disease or condition responsive to human growth hormone receptor antagonists may be breast cancer, central nervous system cancer, melanoma, non-small cell lung cancer, ovarian cancer, prostate cancer, renal cancer, pancreatic cancer, endometrial cancer, meningioma, colorectal cancer, colon cancer, neuroblastoma, stomach cancer, liver cancer, lymphoma, combinations thereof, or any other cancer expressing predetermined amounts of GHR, PRLR, ABC transporters, EMT mediators, or combinations thereof.

The modified human growth hormone receptor antagonist may comprise human growth hormone receptor antagonist G120K wherein two amino acids of human growth hormone receptor antagonist G120K have been changed to cysteine, wherein the two amino acids changed to cysteine are T142 and H151; and a polyethylene glycol molecule conjugated to each substituted cysteine in the human growth hormone receptor antagonist G120K-T151C-T142C, wherein the polyethylene glycol molecules conjugated to the two amino acids changed to cysteine are two 4.5 kDa branched polyethylene glycols each containing three carboxylate anions. The human growth hormone receptor antagonist G120K may have a DNA sequence of SEQ ID NO: 1 and an amino acid sequence of SEQ ID NO: 2. The human growth hormone receptor antagonist G120K-H151C-T142C may have a DNA sequence of SEQ ID NO: 3 and an amino acid sequence of SEQ ID NO: 4. The following amino acid substitutions may be made: H18D, H21N, R167N, K168A, D171S, K172R, E174S, and I179T for preventing binding to a prolactin receptor and this modified composition may be adapted and used for the treatment of acromegaly. The polyethylene glycol molecule may be prepared by stepwise organic chemistry and may be a substantially pure single compound, and the polyethylene glycol molecule may be a branched structure. The polyethylene glycol molecule may contain a maleimide group for conjugation to a free sulfhydryl group.

The anti-cancer composition may be an alkylating agent; an antimetabolite; a plant alkaloid; an antitumor antibiotic; or combinations thereof. The alkylating agent may be chlorambucil, cyclophosphamide, thiotepa, busulfan, cisplatin, or combinations thereof. The antimetabolite may be gemcitabine, 5-fluorouracil, 6-mercaptopurine, cytarabine, or combinations thereof. The plant alkaloid may be vincristine, paclitaxel, etoposide, irinotecan, or combinations thereof. The antitumor antibiotic may be doxorubicin, dactinomycin, mitoxantrone, idarubicin, or combinations thereof. The anti-cancer composition may be a targeted therapy that includes vemurafenib or similar drugs.

Another implementation of the disclosed technology provides another composition and method for treating a disease or condition responsive to human growth hormone receptor antagonists. The composition comprises a modified human growth hormone receptor antagonist, wherein the human growth hormone receptor antagonist comprises human growth hormone receptor antagonist G120K wherein two amino acids of human growth hormone receptor antagonist G120K have been changed to cysteine, wherein the two amino acids changed to cysteine are T142 and H151; and a polyethylene glycol molecule conjugated to each substituted cysteine in the human growth hormone receptor antagonist G120K-H151C-T142C, wherein the polyethylene glycol molecules conjugated to the two amino acids changed to cysteine are two 4.5 kDa branched polyethylene glycols each containing three carboxylate anions, wherein the polyethylene glycol molecule is prepared by step-wise organic chemistry and is a substantially pure single compound, and wherein the polyethylene glycol molecule is a branched structure; and an anti-cancer composition. The method for treating diseases or conditions responsive to human growth hormone receptor antagonists, comprises administering to a patient an effective amount of the composition.

The disease or condition responsive to human growth hormone receptor antagonists may be a cancer that expresses predetermined levels of growth hormone receptor (GHR); predetermined levels of prolactin receptor (PRLR); predetermined levels of both GHR and PRLR); predetermined levels of ATP-binding cassette (ABC)-transporters; or predetermined levels of epithelial to mesenchymal transition (EMT) mediators. The disease or condition responsive to human growth hormone receptor antagonists may be breast cancer, central nervous system cancer, melanoma, non-small cell lung cancer, ovarian cancer, prostate cancer, renal cancer, pancreatic cancer, endometrial cancer, meningioma, colorectal cancer, colon cancer, neuroblastoma, stomach cancer, liver cancer, lymphoma, combinations thereof, or any other cancer expressing predetermined amounts of GHR, PRLR, ABC transporters, EMT mediators, or combinations thereof. The human growth hormone receptor antagonist G120K may have a DNA sequence of SEQ ID NO: 1 and an amino acid sequence of SEQ ID NO: 2. The human growth hormone receptor antagonist G120K-H151C-T142C may have a DNA sequence of SEQ ID NO: 3 and an amino acid sequence of SEQ ID NO: 4. The following amino acid substitutions may be made: H18D, H21N, R167N, K168A, D171S, K172R, E174S, and I179T for preventing binding to a prolactin receptor and this modified composition may be adapted and used for the treatment of acromegaly. The polyethylene glycol molecule may contain a maleimide group for conjugation to a free sulfhydryl group.

The anti-cancer composition may be an alkylating agent; an antimetabolite; a plant alkaloid; an antitumor antibiotic; or combinations thereof. The alkylating agent may be chlorambucil, cyclophosphamide, thiotepa, busulfan, cisplatin, or combinations thereof. The antimetabolite may be gemcitabine, 5-fluorouracil, 6-mercaptopurine, cytarabine, or combinations thereof. The plant alkaloid may be vincristine, paclitaxel, etoposide, irinotecan, or combinations thereof. The antitumor antibiotic may be doxorubicin, dactinomycin, mitoxantrone, idarubicin, or combinations thereof. The anti-cancer composition may be a targeted therapy that includes vemurafenib or similar drugs.

Still another implementation of the disclosed technology provides a method for treating cancer using human growth hormone antagonists, comprising pre-screening a patient by analyzing a tumor biopsy to confirm the presence of cancer and the presence of certain predetermined factors indicative of responsiveness to human growth hormone antagonists; and treating the patient with an effective amount of a composition that includes a modified human growth hormone receptor antagonist and an anti-cancer composition. The certain predetermined factors may include the predetermined levels of Gil R, PRLR, ABC transporters, EMT mediators, insulin-like growth factor-1 (IGF-1); IFG binding protein-3 (IGFBP3), suppressor of cytokine signaling (SOCS_-1, -2, -3; and cytokine inducible SH2 containing protein (CISH). The cancer may be breast cancer, central nervous system cancer, melanoma, non-small cell lung cancer, ovarian cancer, prostate cancer, renal cancer, pancreatic cancer, endometrial cancer, meningioma, colorectal cancer, colon cancer, neuroblastoma, stomach cancer, liver cancer, lymphoma, combinations thereof, or any other cancer expressing predetermined amounts of the predetermined factors.

The modified human growth hormone receptor antagonist may comprise human growth hormone receptor antagonist G120K wherein two amino acids of human growth hormone receptor antagonist G120K have been changed to cysteine, wherein the two amino acids changed to cysteine are T142 and H151; and a polyethylene glycol molecule conjugated to each substituted cysteine in the human growth hormone receptor antagonist G120K-H151C-T142C, wherein the polyethylene glycol molecules conjugated to the two amino acids changed to cysteine are two 4.5 kDa branched polyethylene glycols each containing three carboxylate anions. The human growth hormone receptor antagonist G120K may have a DNA sequence of SEQ ID NO: 1 and an amino acid sequence of SEQ ID NO: 2. The human growth hormone receptor antagonist G120K H151C-T142C may have a DNA sequence of SEQ ID NO: 3 and an amino acid sequence of SEQ ID NO: 4. The polyethylene glycol molecule may be prepared by step-wise organic chemistry and may be a substantially pure single compound, and the polyethylene glycol molecule may be a branched structure. The polyethylene glycol molecule may contain a maleimide group for conjugation to a free sulfhydryl group.

The anti-cancer composition may be an alkylating agent; an antimetabolite; a plant alkaloid; an antitumor antibiotic; or combinations thereof. The alkylating agent may be chlorambucil, cyclophosphamide, thiotepa, busulfan, cisplatin, or combinations thereof. The antimetabolite may be gemcitabine, 5-fluorouracil, 6-mercaptopurine, cytarabine, or combinations thereof. The plant alkaloid may be vincristine, paclitaxel, etoposide, irinotecan, or combinations thereof. The antitumor antibiotic may be doxorubicin, dactinomycin, mitoxantrone, idarubicin, or combinations thereof. The anti-cancer composition may be a targeted therapy that includes vemurafenib or similar drugs.

BRIEF DESCRIPTION OF THE DRAWINGS

The accompanying figures, which are incorporated into and form a part of the specification, schematically illustrate one or more example implementations of the disclosed inventive subject matter and, together with the general description given above and detailed description given below, serve to explain the principles of the disclosed subject matter, and wherein:

FIGS. 5A(1)-5A(6) show the effect of GHR antagonists on the expression of six ABC transporters in a melanoma cell line, wherein FIG. 5A(1) includes data for MALME-3M—ABCB1, FIG. 5A(2) includes data for MALME-3M—ABCB8, FIG. 5A(3) includes data for MALME-3M—ABCC-1, FIG. 5A(4) includes data for MALME-3M—ABCC2, FIG. 5A(5) includes data for MALME-3M—ABCG1, and FIG. 5A(6) includes data for MALME-3M—ABCG2;

FIGS. 5B(1)-5B(9) show the effect of GHR antagonists on the expression of nine EMT markers in a melanoma cell line, wherein FIG. 5B(1) includes data for MALME-3M—FGFBP1, FIG. 5B(2) includes data for MALME-3M—CDH1, FIG. 5B(3) includes data for MALME-3M—CLDN1, FIG. 5B(4) includes data for MALME-3M—ZEB1, FIG. 5B(5) includes data for MALME-3M—CDH2, FIG. 5B(6) includes data for MALME-3M—EPAS1, FIG. 5B(7) includes data for MALME-3M—SNAI1, FIG. 5B(8) includes data for MALME-3M—SNAI2, and FIG. 5B(9) includes data for MALME-3M—VIM;

FIGS. 7A, 7B, and 7C(1)-7C(8) show the effect of GHR antagonists [Peg=pegvisomant, G=Compound G] on drug efflux rate (FIG. 7A), percentage of drug retention (FIG. 7B), and fluorescent images after a fluorescent drug surrogate (DiOC2) has been loaded into pancreatic cancer cells using an in vitro multidrug efflux assay method (n=3, * indicates $p<0.05$) (FIGS. 7C(1)-7C(8)), wherein GH increases the tumor cell drug efflux rate (decreases drug retention in tumor cells) while the GHR antagonists significantly suppress it;

DETAILED DESCRIPTION

Figure 1:
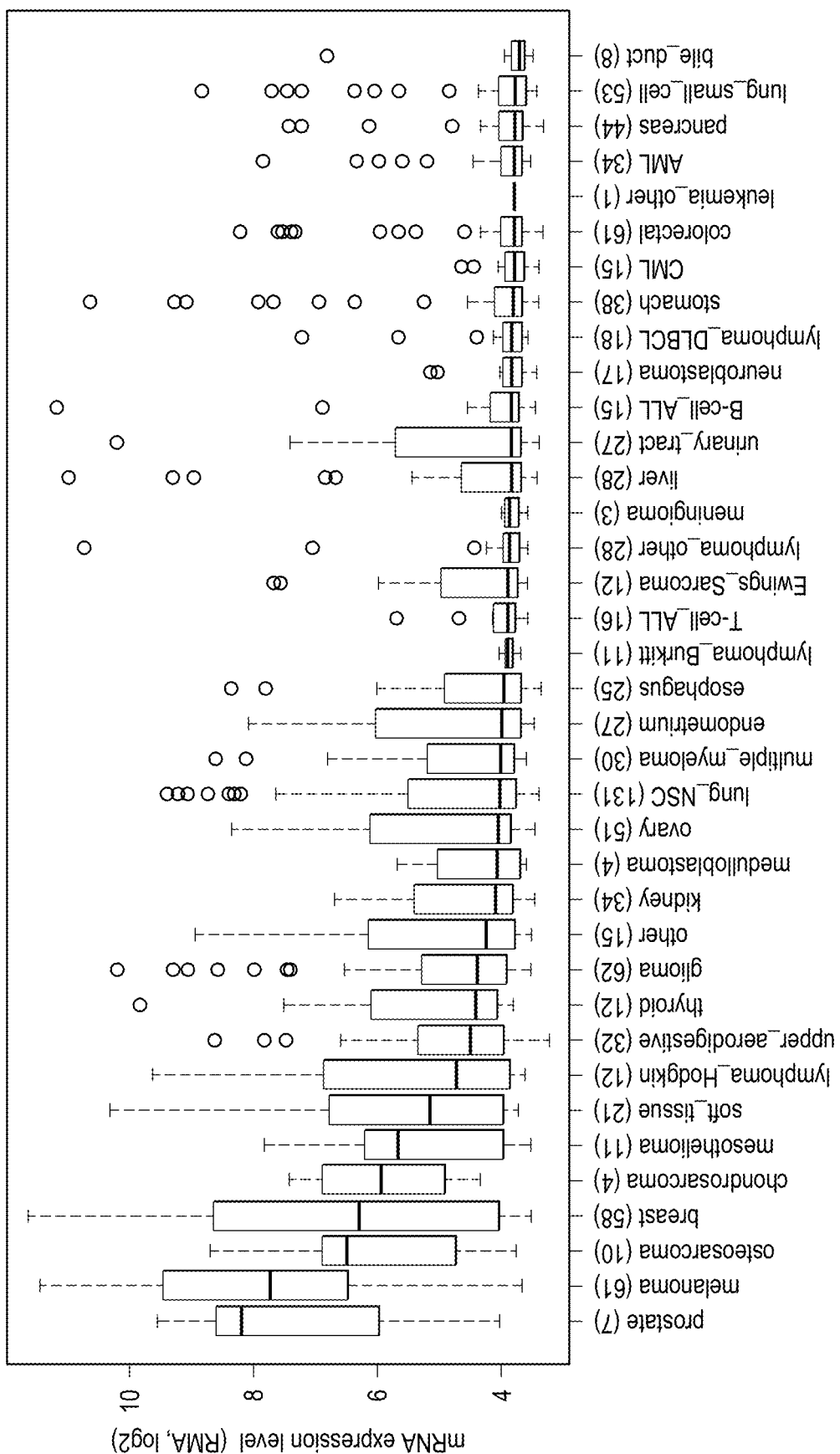
FIG. 1 is a bar chart depicting the level of GHR mRNA expression in multiple cell lines from thirty-seven (37) cancer cell types, which are listed along the x-axis of the chart.

Example implementations are now described with reference to the Figures. Reference numerals are used throughout the detailed description to refer to the various elements and structures. Although the following detailed description contains many specifics for the purposes of illustration, a person of ordinary skill in the art will appreciate that many variations and alterations to the following details are within the scope of the disclosed inventive subject matter. Accordingly, the following implementations are set forth without any loss of generality to, and without imposing limitations upon, the claimed subject matter.

The following abbreviations, which are used throughout this application, have the following specific meanings. DPEG®-A refers to MAL-DPEG®$_{12}$-Tris(DPEG®$_{24}$-acid)$_3$ (Quanta BioDesign #1145). Compound G or G refers to hGHR antagonist hGH-G120K having T142 and H151 changed to cysteine and having both added cysteines conjugated with DPEW®-A. Compound D or D refers to hGHR antagonist hGH-G120K having T142 changed to cysteine and having the added cysteine conjugated with a 40 kDa branched polyethylene glycol. Peg refers to SOMAVERT® (pegvisomant) and Dox refers to doxorubicin. The disclosed technology includes compositions and methods for treating cancer patients who are identified by expression of GHR, PRLR, selected ABC drug efflux pumps, selected EMT modulators, IGF-1, IGFBP3, SOCS-1, or CISH., wherein treatment comprises administering to the patient an effective dose of a chemotherapeutic drug combined with an effective dose of Compound G.

GHR Expression in Cancer Cell Lines

The effectiveness of an hGHR antagonist for cancer treatment, either by itself or in combination with a cancer drug, is related closely to the expression of the hGHR by a particular cancer. When the hGHR antagonist is also an antagonist of the PRLR, then the level of PRLR expression will also determine the susceptibility of a cancer to this treatment. It was previously observed that most of 60 cell lines from nine cancer types expressed high levels of either the hGHR, the PRLR, or both receptors [5]. Analysis of the levels of GHR mRNA expression from 37 cancer types (see FIG. 1), with between 4 and 131 cell lines included for each cancer, indicated that almost all of the cancer types had high hGHR expression for at least a subset of the individual cancers tested.

Figure 2A:
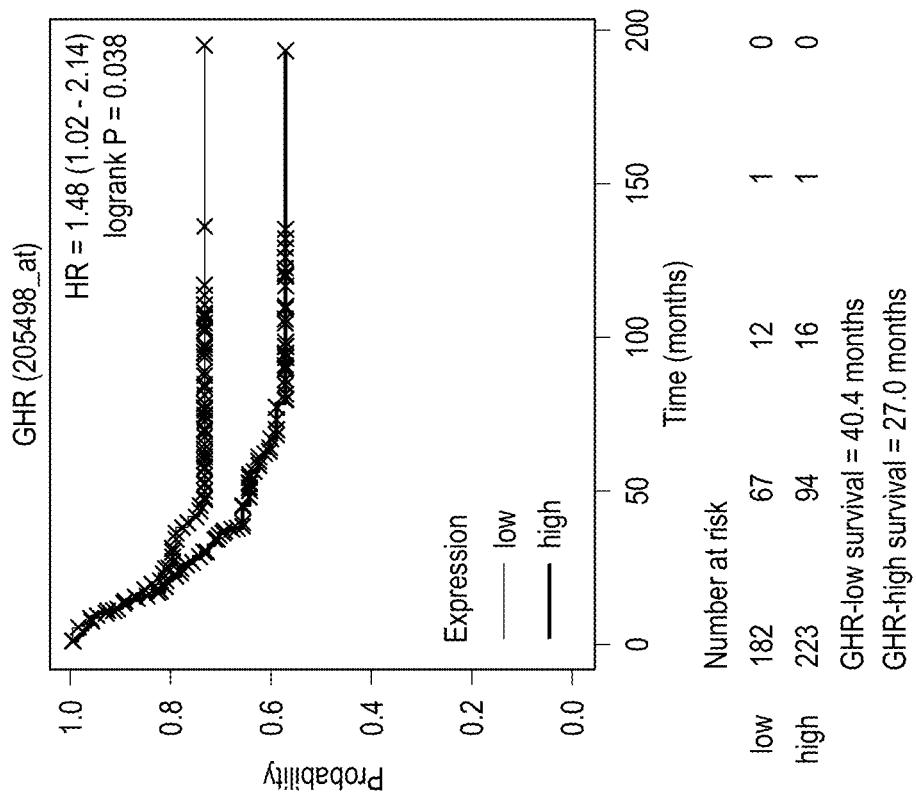
FIGS. 2A-2C are plots for two breast cancer subtypes (triple-negative and HER2-enriched breast cancers) showing the differences in patient overall survival (in months) for cancers with low and high growth hormone receptor (GHR) expression levels, wherein FIG. 2A includes data for subtype HER2 enriched (ER-PR-HER+) breast cancer (n=96), wherein FIG. 2B includes data for subtype triple-negative breast cancer (n=405), and wherein FIG. 2C includes data for subtype triple-negative breast cancer chemotherapy-treated (n=227)
Figure 2B:
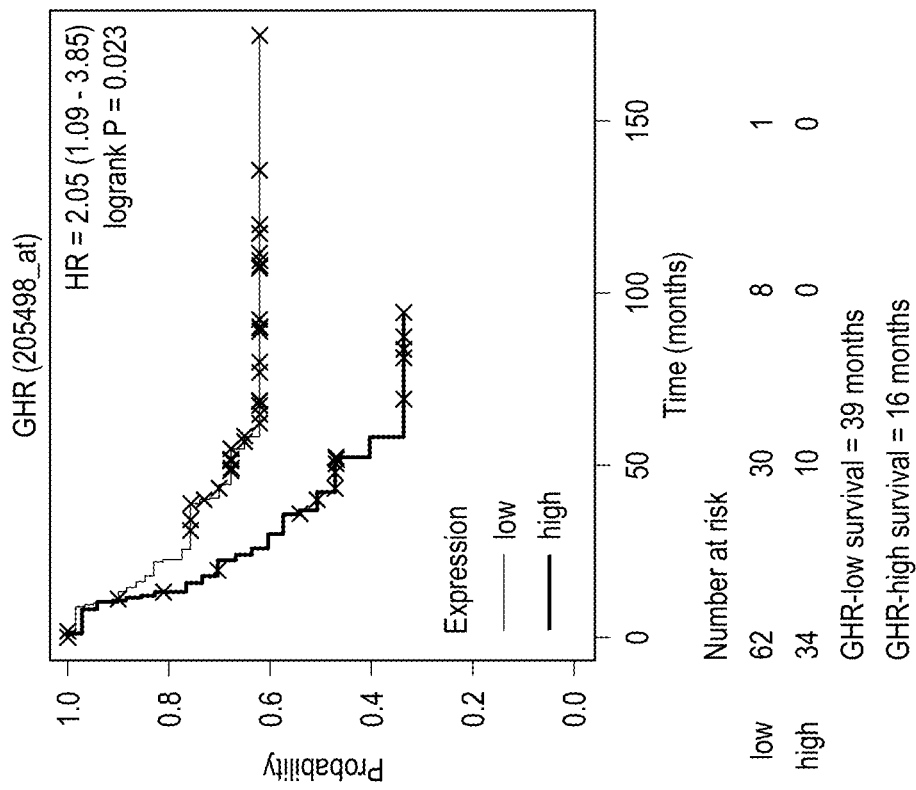
Figure 2C:
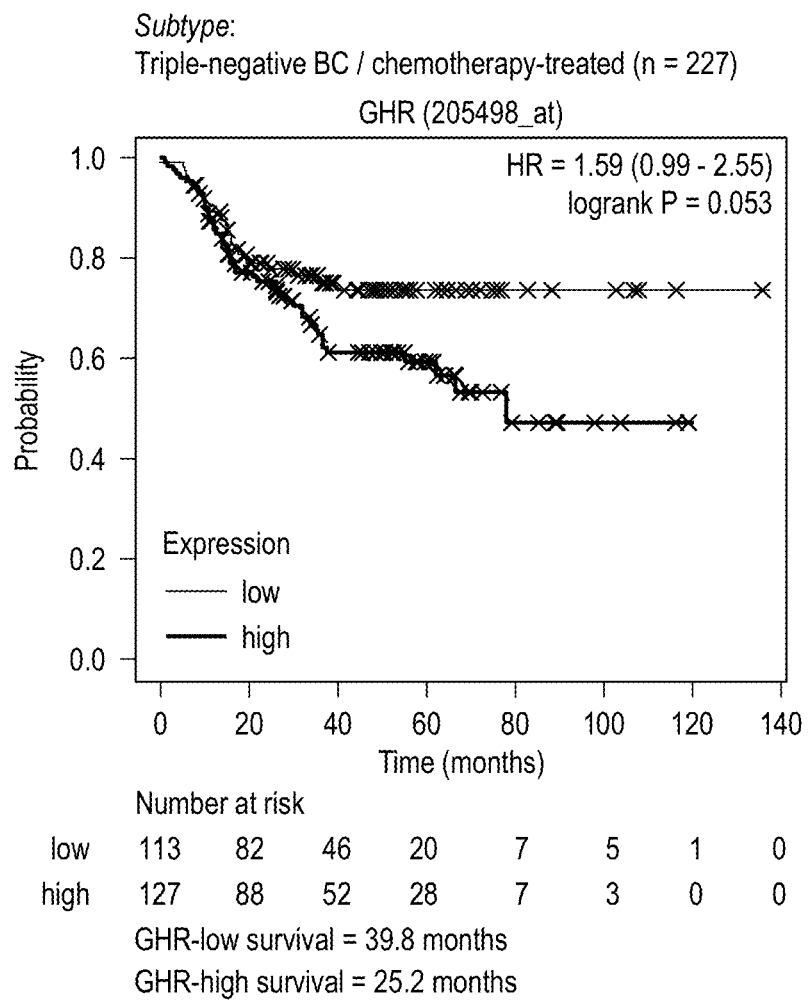
Figure 3A:
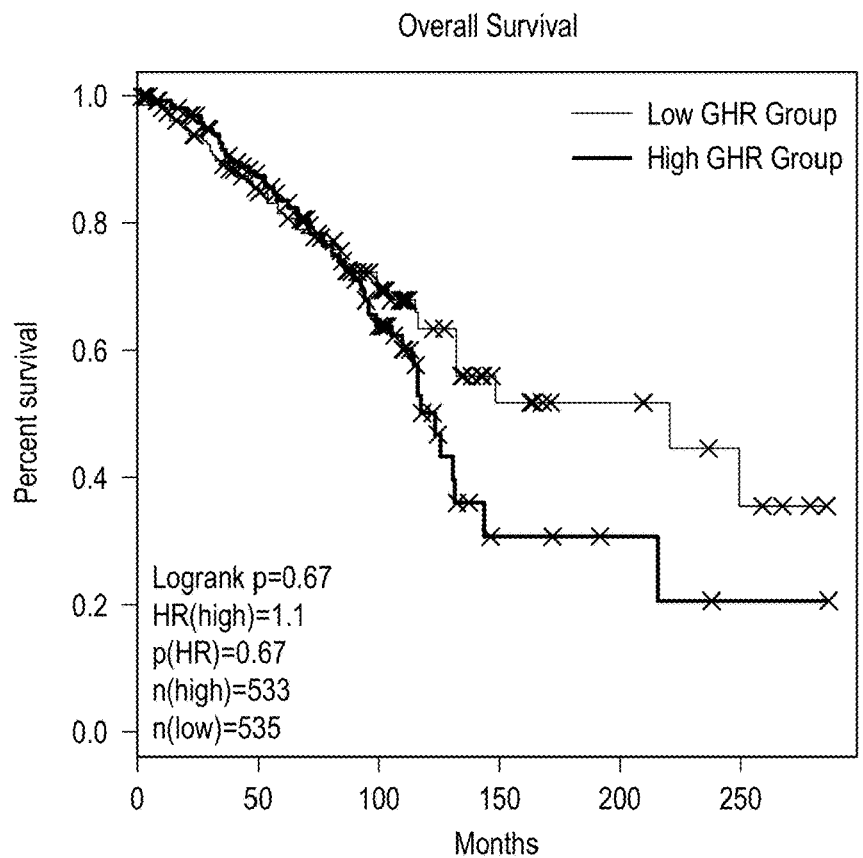
FIGS. 3A-3D are graphs showing the relationship between overall survival for breast cancer (BC) patients (ungrouped/all) with specific gene expression in the Cancer Genome Atlas (TCGA) breast cancer database, wherein data for patients with high GHR expression (FIG. 3A) or high PRLR expression (FIG. 3B) had a poorer survival compared to low GHR or low PRLR expression groups, and wherein in breast cancer patients with high expression of both GHR and PRLR (FIG. 3C), or with high expression of GH,GHR, and PRLR (FIG. 3D), survival was significantly poorer than the corresponding low expression cohorts of the same gene-sets (processed using GEPIA2)
Figure 3B:
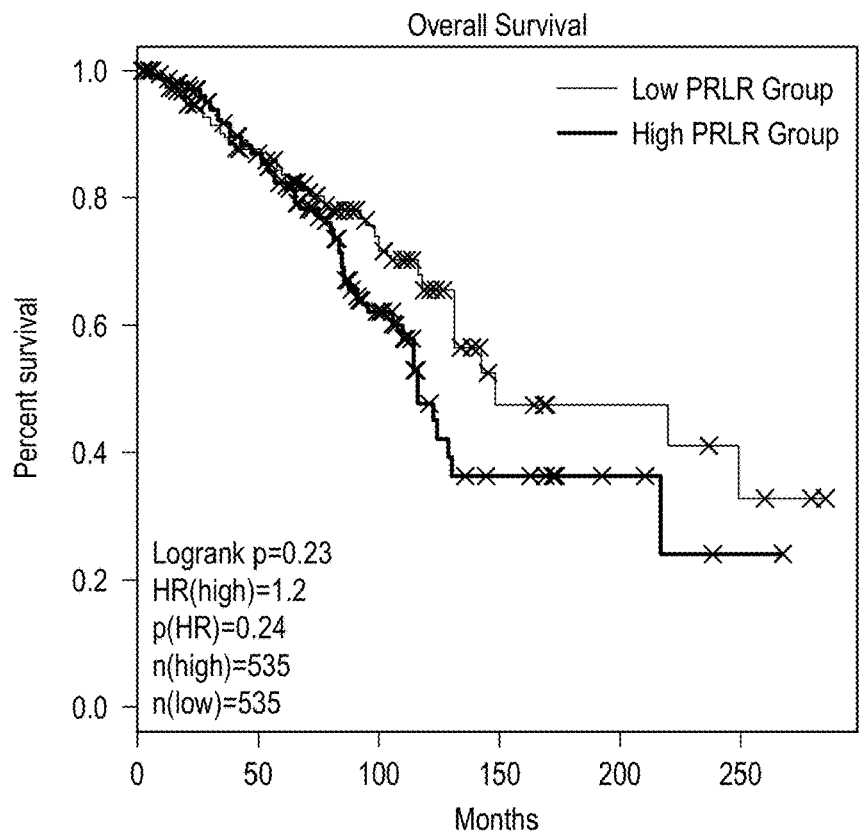
Figure 3C:
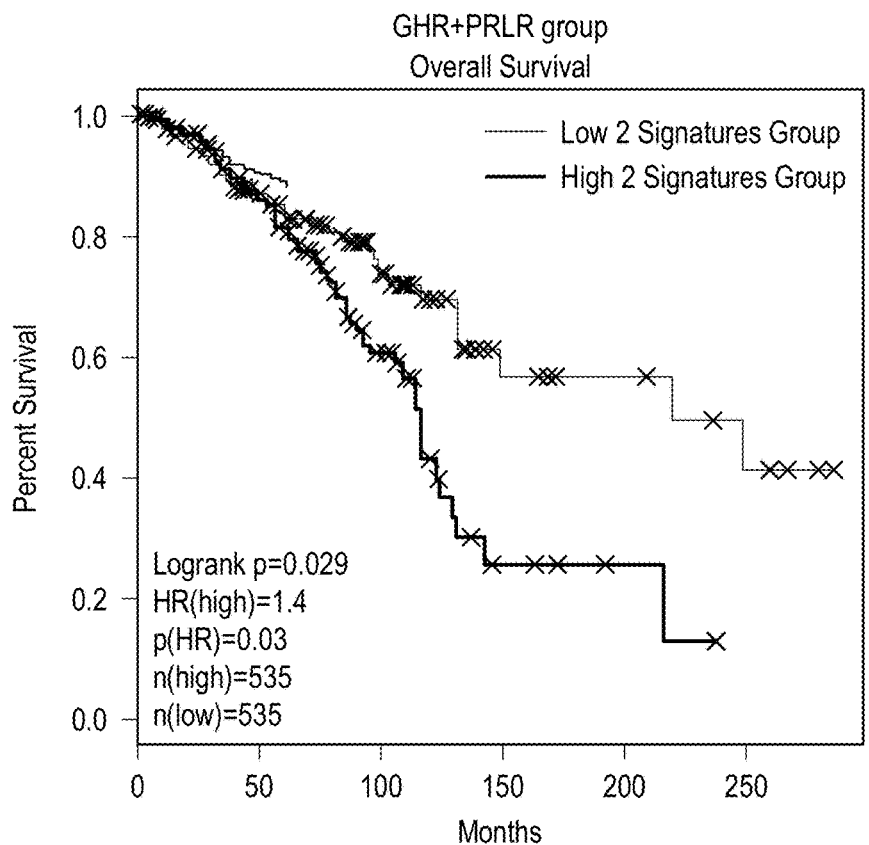
Figure 3D:
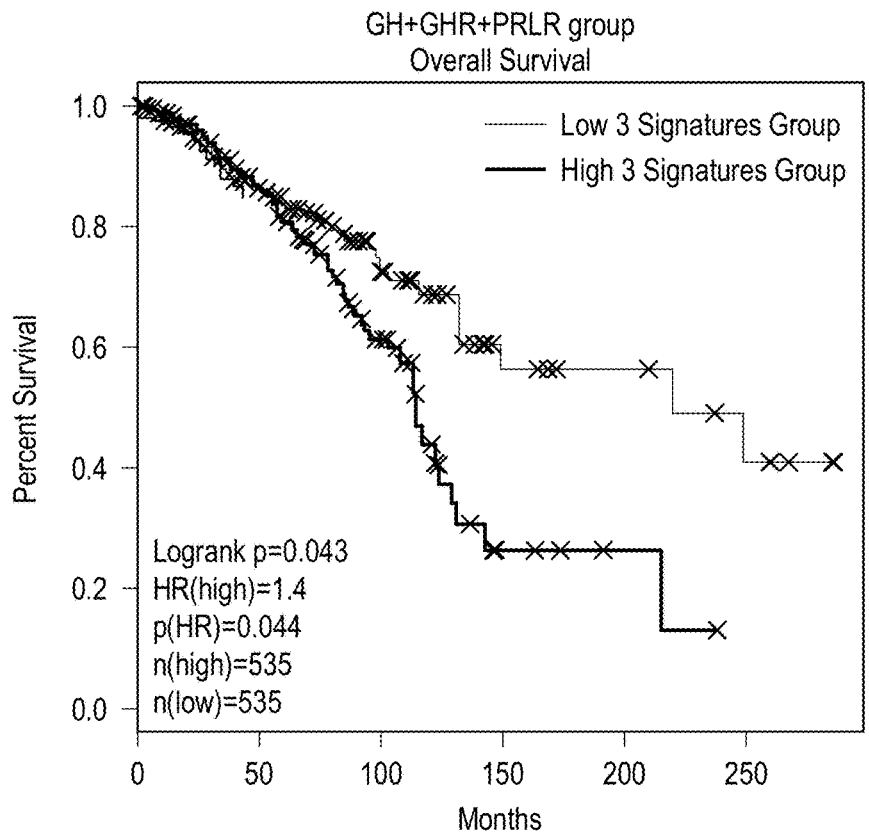

The level of hGHR expression across multiple human patient datasets correlates with decreased patient survival for HER2 enriched breast cancer and triple-negative breast cancer (see FIGS. 2A-2C). FIGS. 3A-3D illustrate that breast cancer patients with increased levels of both GHR+PRLR expression or GH+GHR+PRLR expression have lower percent survivals than high levels of GH or GHR or PRLR expression alone.

GHR Expression and the Expression of ABC Transporters and EMT Markers

Figure 4A:
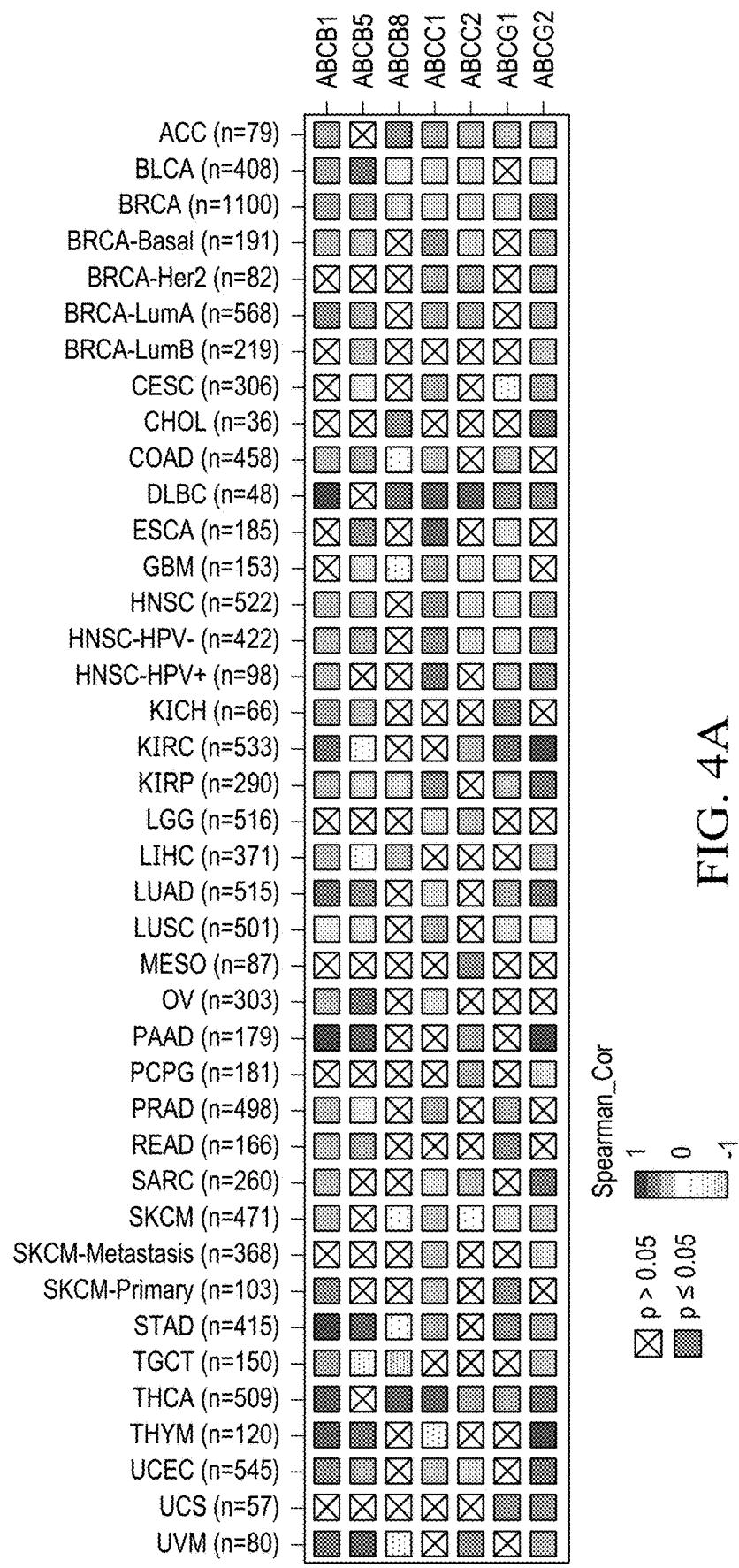
FIG. 4A is a heatmap showing a Spearman correlation coefficient between GHR expression and ABC type multi-drug transporter expression across forty (40) different cancer types from human patients in The Cancer Genome Atlas (TCGA) database, wherein the heatmap indicates a consistent positive (red) correlation between GHR expression and ABC type multidrug transporters.
Figure 4B:
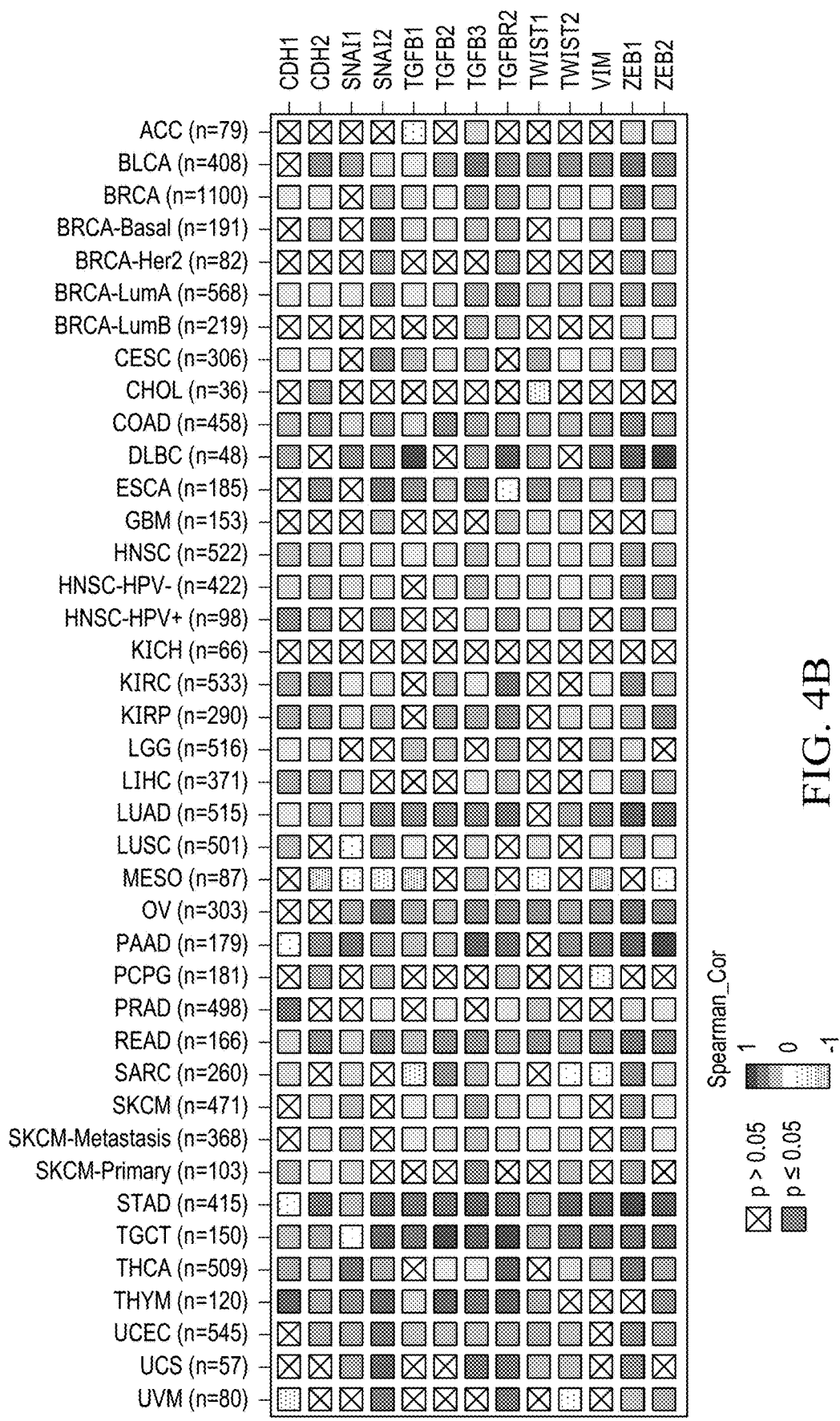
FIG. 4B is a heatmap showing a Spearman correlation coefficient between GHR expression and known EMT markers expression across forty (40) different cancer types from human patients in the TCGA database, wherein the heatmap indicates a consistent positive (red) correlation between GHR and markers of EMT across majority of cancer types.
Figure 6A:
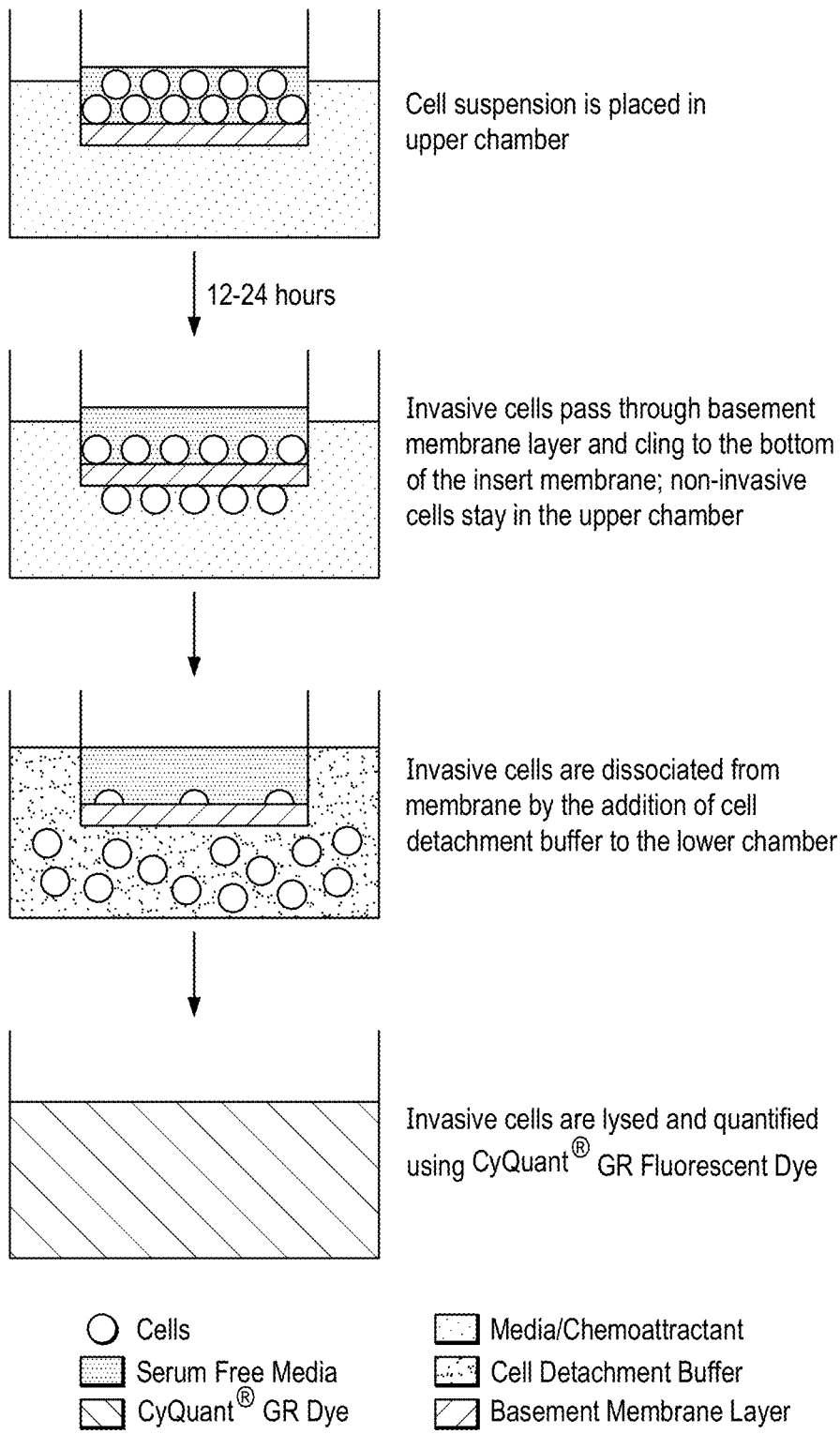
FIGS. 6A-6D show the effect of GHR antagonists (Peg=SOMAVERT® (pegvisomant), G=Compound G) on a basement membrane invasion assay (in vitro) (FIG. 6A) using three pancreatic cancer cell lines (n=3, * indicates $p<0.05$), wherein GH increases the tumor cell invasion rate while the GHR antagonists significantly suppress it, and wherein FIG. 6B includes data for invasion assay—BxPC3, FIG. 6C includes data for invasion assay—PANC1, and FIG. 6B includes data for invasion assay—LTPA.
Figure 6B:
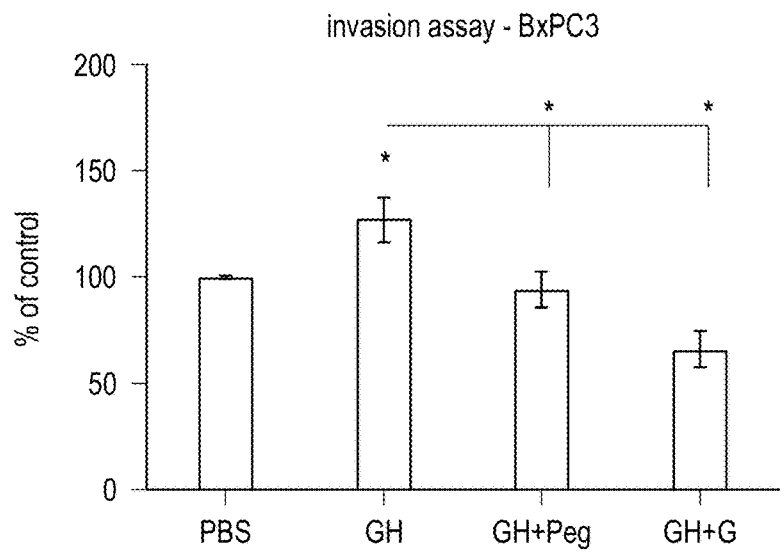
Figure 6C:
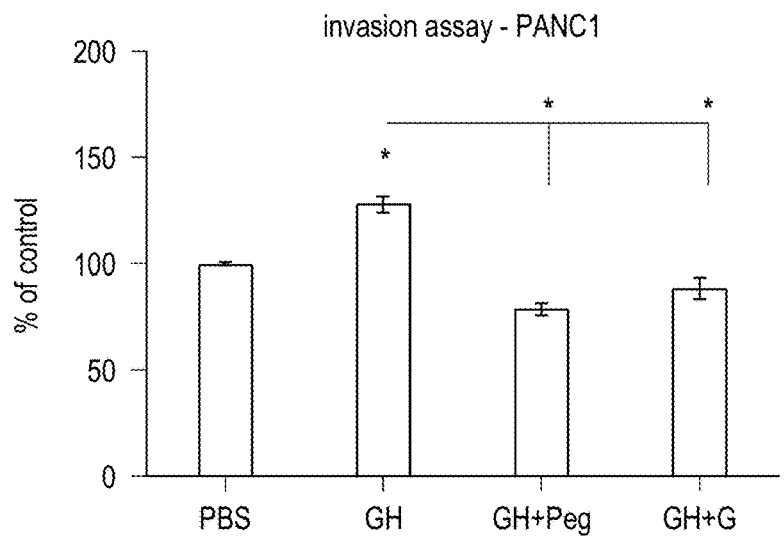
Figure 6D:
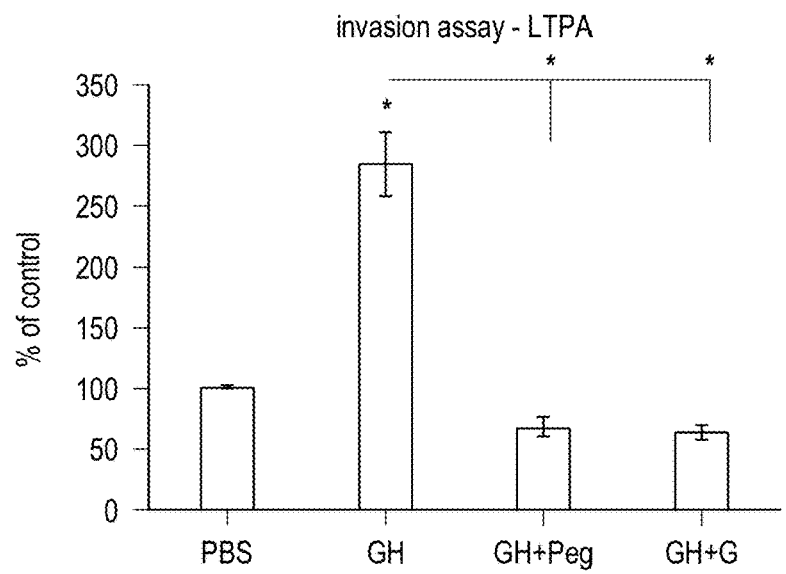

FIG. 4A shows a correlation across 40 different cancer cell types between GHR expression and the expression of ABC transporters across all patients in the TCGA database. FIG. 4B shows the same correlation between GHR expression and the expression of EMT mediators. Because upregulation of ABC transporters and EMT mediators lead to chemotherapy resistance, these Figures shows that chemotherapy resistance is associated with GHR expression.

The effect of GHR antagonists on the expression of six ABC transporters in a melanoma cell line is shown in FIGS. 5A(1)-5A(6). When used as a monotherapy, Compound G significantly reduces the expression of four of the six ABC transporters. When GH or doxorubicin is present, Compound G also reduces the expression of four ABC transporters. When both GH and doxorubicin are added, Compound G greatly reduces the expression of all six ABC transporters. This observation is due to the fact that the expression of ABC transporters is enhanced in presence of GH or doxorubicin or both GH and doxorubicin.

The effect of hGHR antagonists on the expression of nine EMT markers in a melanoma cell line is shown in FIGS. 5B(1)-5B(9). When used as a monotherapy, Compound G significantly reduces the expression of multiple EMT mediators. When GH or doxorubicin or both are present, Compound G also reduces the expression of multiple EMT mediators, presumably because the expression of EMT mediators is significantly enhanced in presence of GH or doxorubicin or both GH and doxorubicin.

FIGS. 6A-6D show the effect of the hGHR antagonists Compound G and SOMAVERT® (pegvisomant) on a basement membrane invasion assay using three pancreatic cancer cell lines. This assay quantifies the ability of cells to migrate through a membrane, a property of cells that have transitioned from epithelial cells to mesenchymal cells. For all three cell lines, the addition of GH increases cell migration. This effect of GUI is blocked by the addition of either SOMAVERT® (pegvisomant) or Compound G.

The Effect of hGHR Antagonists on Drug Efflux

Figure 7A:
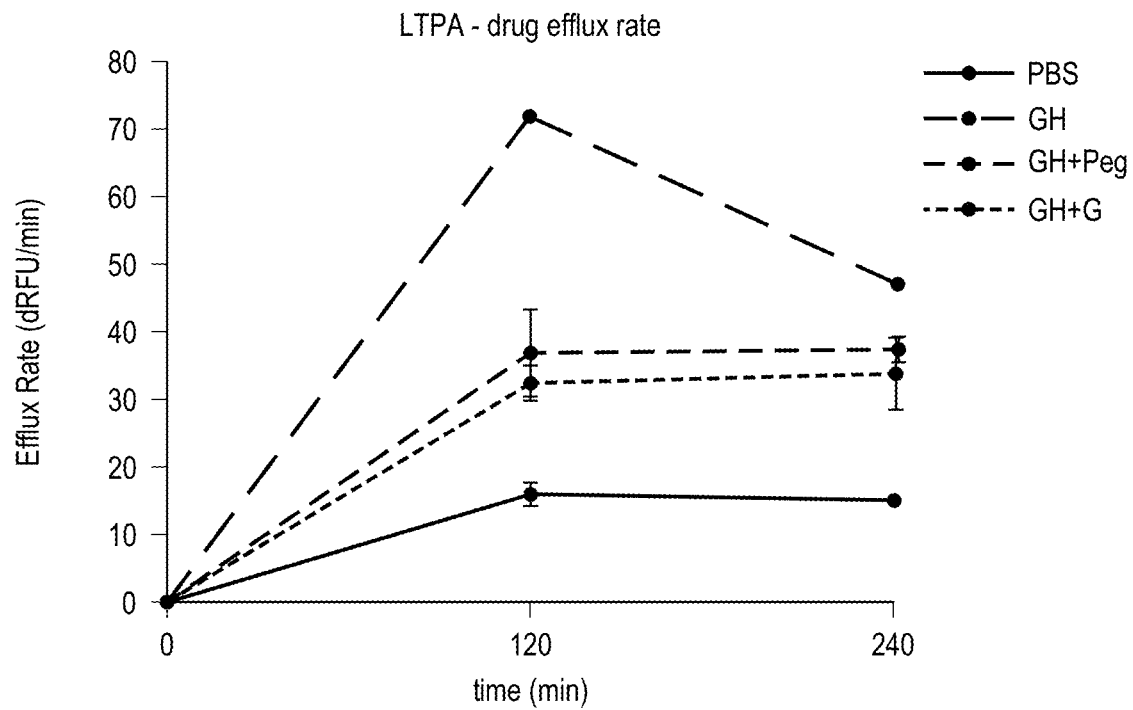
Figure 7B:
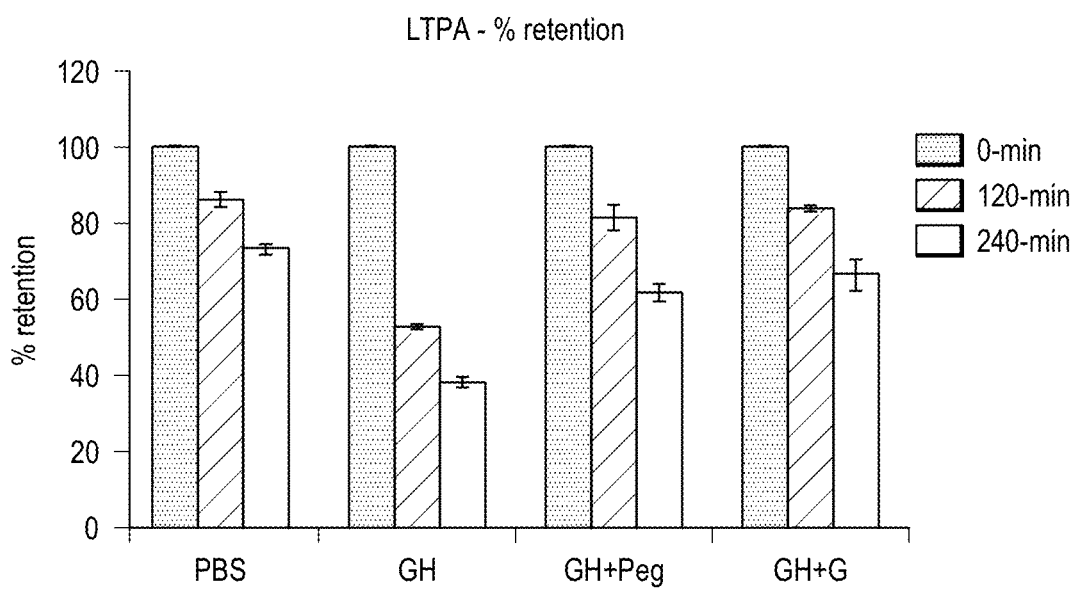

The effect of hGHR antagonists on the drug efflux rate, using DiOC2 dye as a drug surrogate, from pancreatic cancer cells is shown in FIGS. 7A-7C. With reference to FIG. 7A, after 120 minutes, the efflux rate with GH addition is approximately four-fold greater than the efflux rate with no additives (PBS). In the presence of GH+Pegvisomant or GH+Compound G, the efflux rate is markedly suppressed compared with GH alone by a factor of approximately two. FIG. 7B, illustrates the effect of hGHR antagonists on the percentage of drug retention from pancreatic cancer cells. In the PBS control, approximately 85% of the drug is retained after 120 minutes. The retention after 120 minutes decreases to ~54% in the presence of GH but increases to ~83% in the presence of GH plus Compound G or GH plus Pegvisomant. Finally, FIGS. 7C(1)-7C(8) provides fluorescent images of a labeled drug after being loaded into pancreatic cancer cells and incubated for 0 minutes and 120 minutes in PBS (FIG. 7C(1)-FIG. 7C(2)), GH (FIG. 7C(3)-FIG. 7C(4)), GH+Pegvisomant (FIG. 7C(5)-FIG. 7C(6)), or GH+Compound G (FIG. 7C(7)-FIG. 7C(8)). In FIGS. 7C(1)-7C(8), the fluorescence of the cells at 0 minutes is different for the four different conditions, so the drug remaining after 120 minutes (fluorescence) was compared with its own 0 min control. It is clear from the images that the cells treated with GH+Compound G retain the greatest amount of drug.

Figure 8:
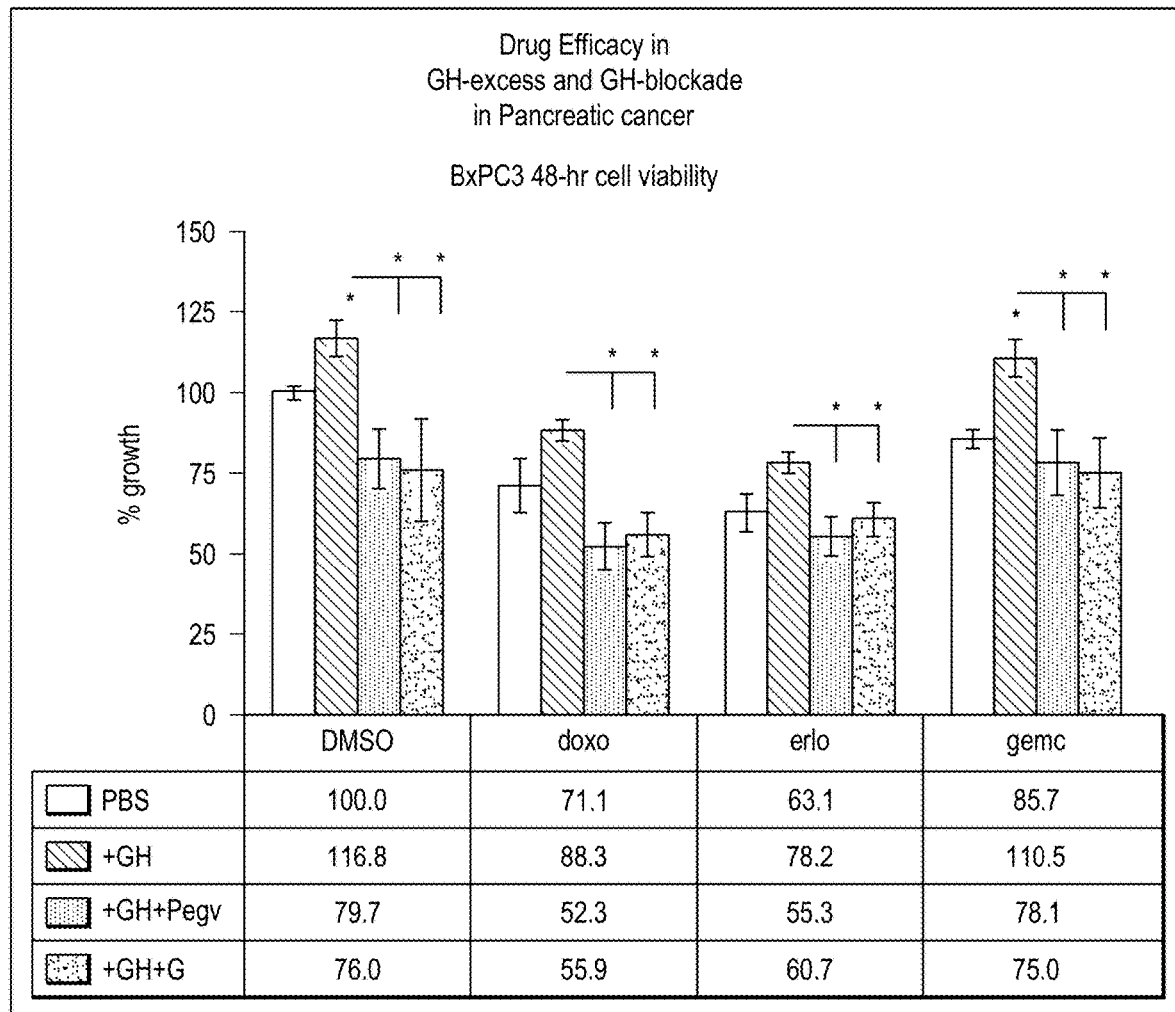
FIG. 8 shows the viability of pancreatic cancer cells when incubated in the presence anti-cancer drugs and either PBS, GH, GH+SOMAVERT® (pegvisomant), or GH+Compound G, wherein the anti-cancer drugs used were doxorubicin (doxo), erlotinib (erlo), or gemcitabine (gemc), and the control was DMSO.

FIG. 8 illustrates the viability of pancreatic cancer cells when incubated in the presence of anti-cancer drugs and either buffer (PBS), GH, GH+SOMAVERT® (pegvisomant), or GH+Compound G. The anti-cancer drugs are doxorubicin (doxo), erlotnib (erlo), or gemcitabine (gemc) and the control is DMSO, the vehicle for the anti-cancer drugs. In all cases, the addition of GH increases the cell viability. However, the addition of either SOMAVERT'

(pegvisomant) or Compound G to the GH reduces the viability, in all cases, to below that of PBS.

The Effect of GHR Antagonists+Anti-Cancer Drugs on Pancreatic Tumor Xenografts

Figure 9A:
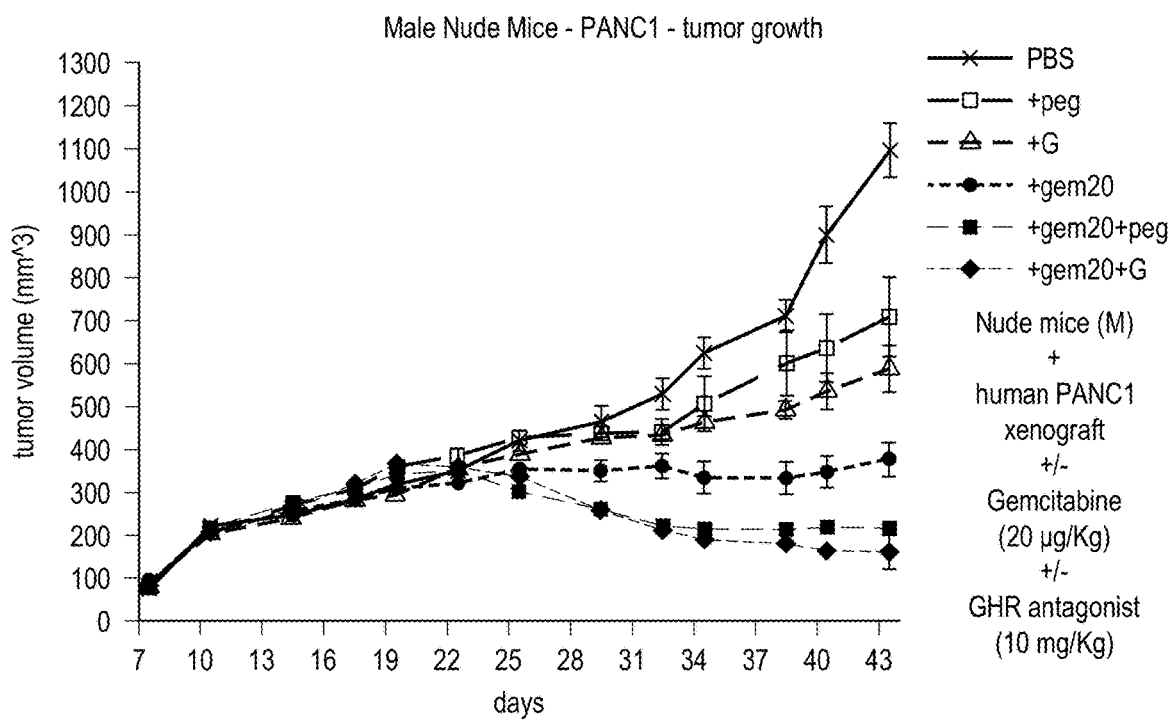
FIG. 9A is a graph showing the effect of different treatments on the growth (tumor volume) of human pancreatic cancer (PANC1) xenografts implanted in male nude mice, wherein the hGHR antagonists were SOMAVERT® (pegvisomant) (peg) and compound-G (G) treated at 10 mg/kg/day while gem20=gemcitabine was treated at 20 mg/kg every 3 days, wherein all treatments started at day-17 and were by intra-peritoneal injections, and wherein gemcitabine, SOMAVERT® (pegvisomant), or compound-G by themselves were effective in decreasing tumor growth rate when used as monotherapy; however, combinations of gem20+peg or gem20+G were significantly more efficacious than gem20 or peg or G alone.

Specific volumes of pancreatic tumor xenografts implanted in male nude mice after treatment with hGHR antagonists (10 mg/kg/day), gemcitabine (20 mg/kg/3-days) and combinations of the antagonists+gemcitabine are shown in FIG. 9A. Treatments started at day-17. Both of the hGHR antagonists ((SOMAVERT® (pegvisomant) and Compound G)) significantly decrease the tumor volume relative to that of the PBS control by day-30 (13 days after start of treatment). However, for both of these antagonists, the tumor volume continues to increase. Gemcitabine alone shows a greater reduction of tumor volume compared to the hGHR antagonists, but the absolute tumor volume appears to resume trending upwards by day-43. The combinations of gemcitabine+SOMAVERT® (pegvisomant) and gemcitabine+Compound G show the greatest reduction of tumor volume. After day-43 (26 days of treatment) there is no indication that the tumor volume has begun to increase using the combination treatments. The combination of Compound G+gemcitabine gave the greatest tumor volume reduction.

Figure 9B:
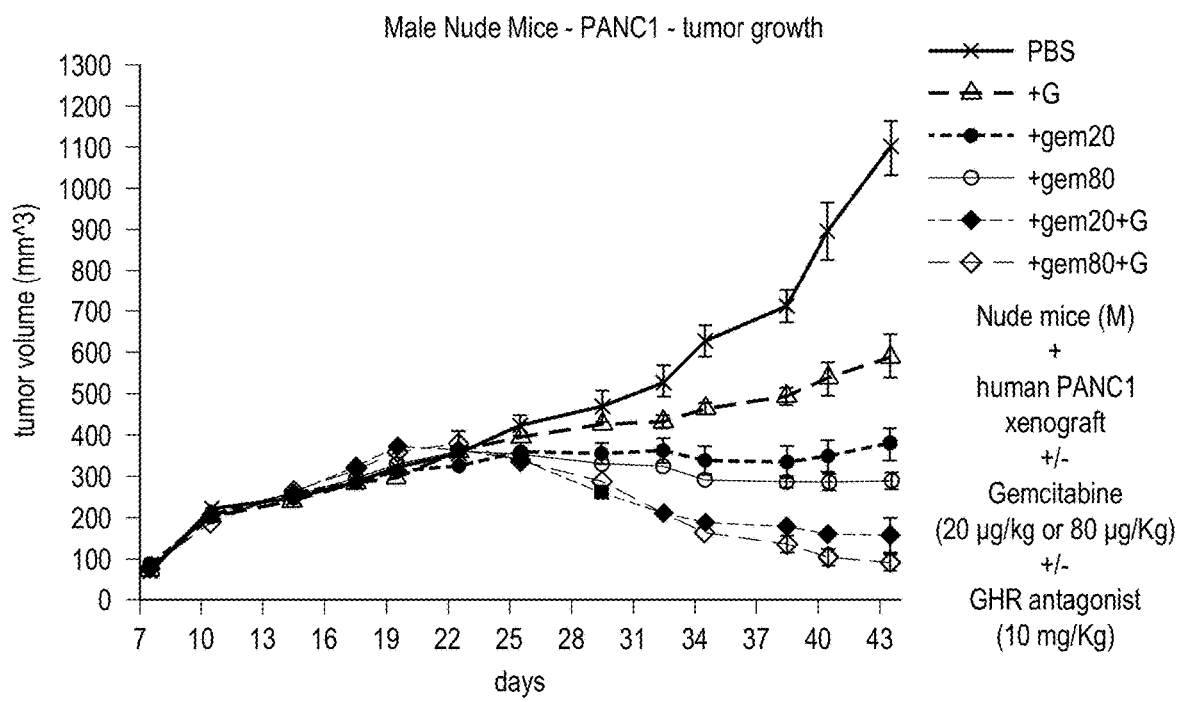
FIG. 9B is a graph showing the effect of different treatments on the growth (tumor volume) of human pancreatic cancer (PANC1) xenografts implanted in male nude mice, wherein the hGHR antagonist was compound-G (G) treated at 10 mg/kg/day while gem20=gemcitabine was treated at 20 mg/kg every 3 days, or gem80=gemcitabine was treated at 80 mg/kg every 3 days, wherein all treatments started at day 17 and were by intra-peritoneal injections, wherein both doses of gemcitabine or compound-G were effective in decreasing tumor growth rate when used as monotherapy; however, combinations of gem20+G or gem80+G were significantly more efficacious than gem20 or gem80 or G alone, and wherein Gem20+G was more efficacious than Gem20, while Gem80+G was more efficacious than Gem80 alone and Gem20+G was better than Gem80 alone.

FIG. 9B shows the volume of pancreatic tumor xenografts implanted in male nude mice after treatment with 80 mg/kg/3-days gemcitabine and Compound G (10 mg/kg/day)+80 mg/kg/3-days gemcitabine. The plots for PBS, Compound G (10 mg/kg/day) alone, gemcitabine (20 mg/kg/3-days) alone, or Compound G (10 mg/kg/day)+gemcitabine (20 mg/kg/3-days), which are taken from FIG. 9A, are also included in FIG. 9B. Gemcitabine by itself at 80 mg/kg/3-days does not decrease the tumor volume significantly beyond that obtained with 20 mg/kg/3-day dose of the same drug and, for the 80 mg/kg/3-day regimen, the tumor volume appears to have plateaued by day-43 (26 days of treatment). The 80 mg/kg/3-days Gemcitabine+mg/kg/day Compound G caused the maximum tumor volume reduction of all conditions, and the tumor volume appears to be still decreasing at the final day of the study (day-43).

Figure 10:
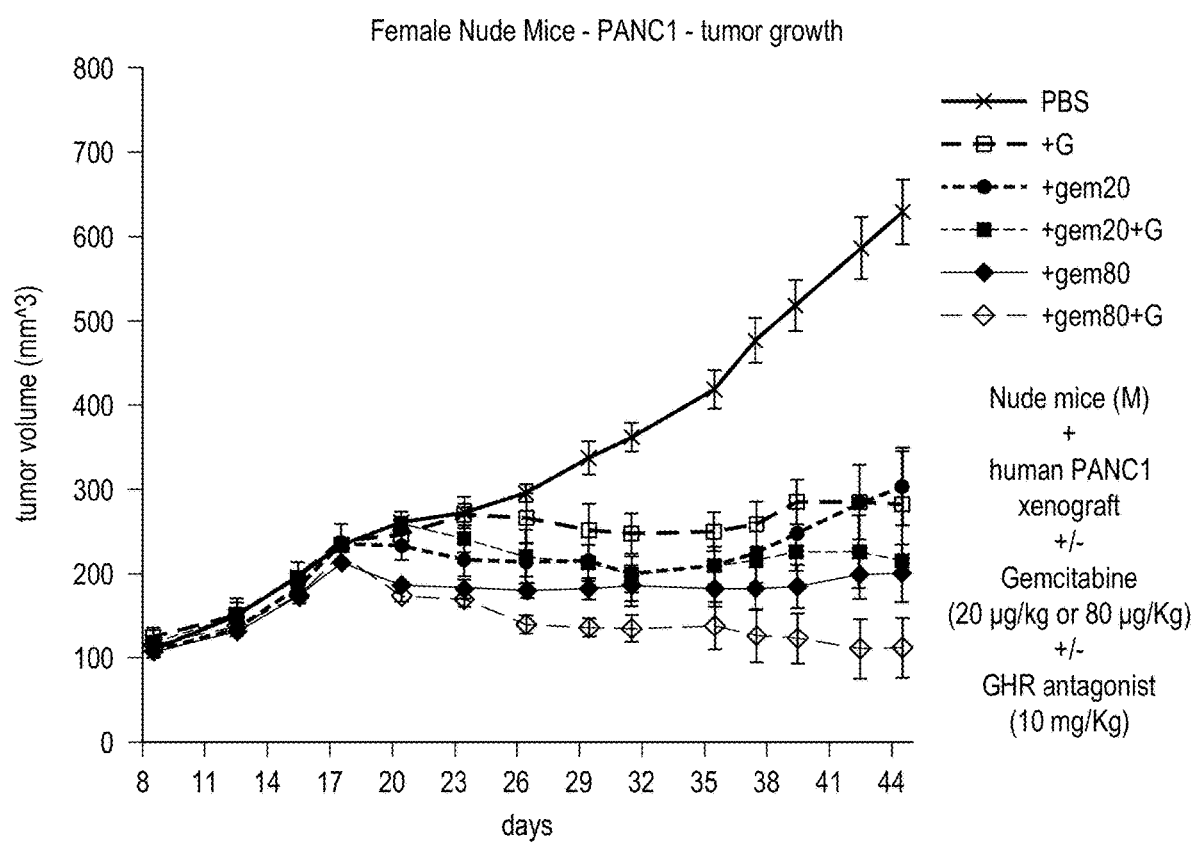
FIG. 10 is a graph showing the effect of different treatments on the growth (tumor volume) of human pancreatic cancer (PANC1) xenografts implanted in female nude mice, wherein the hGHR antagonist is compound-G (G) treated at 10 mg/kg/day while gem20=gemcitabine treated at 20 mg/kg every 3 days or gem80=gemcitabine treated at 80 mg/kg every 3 days, wherein all treatments started at day-17 and were by intra-peritoneal injections, and wherein both doses of gemcitabine or compound-G were effective in decreasing tumor growth rate when used as monotherapy; however, combinations of gem20+G or gem80+G were significantly more efficacious than gem20 or gem80 or G alone, wherein. Gem20+G was more efficacious than Gem20 while Gem80+G was more efficacious than Gem80 alone and Gem20+G was as efficacious as Gem80 alone.

FIG. 10 shows the volume of pancreatic tumor xenografts implanted in female nude mice after treatment with either Compound-G (10 mg/kg/day) alone, or gemcitabine (20 or 80 mg/kg/3-days) alone, or Compound G (10 mg/kg/day)+20 mg/kg/3-days gemcitabine, or Compound G (10 mg/kg/day)+80 mg/kg/3-days gemcitabine. Treatment started at day-17. After days of treatment (day-42 of study), the tumor reduction due to 20 mg/kg/3-days gemcitabine alone or Compound G (10 mg/kg/day) alone are almost equivalent but only the gemcitabine treated mice show tumor volumes that are trending higher, indicating onset of chemoresistance. The combination of Compound G (10 mg/kg/day)+20 mg/kg/3-days gemcitabine reduces the tumor volume growth drastically and the tumor volume does not appear to trend upwards through the end of the study (day-44). Gemcitabine at 80 mg/kg/3-days alone shows the same tumor reduction at day-44 as Compound G (10 mg/kg/day)+20 mg/kg/3-days gemcitabine. Compound G (10 mg/kg/day)+80 mg/kg/3-days gemcitabine shows the greatest inhibition of tumor growth, which appears to be still decreasing after 44 days (end of study), at which point 3 of 8 animals in the group were tumor-free.

Personalized Medicine/Precision Medicine Preliminary Diagnostic Test

One implementation of the disclosed technology includes a preliminary molecular analysis of a tumor biopsy sample to determine if a patient is a suitable candidate for treatment with the disclosed combination therapy. This analysis involves analyzing expression levels of a predetermined set genes where specific changes in the expression levels of these genes correlates with the biological activities affected by the disclosed combination therapy. More specifically, identification of elevated levels of expression of selected genes is used to identify patients that are proper candidates for treatment with the GHR antagonist plus cancer therapeutic agent.

Genes whose expression levels are key indicators of effective responsiveness to the disclosed GHR antagonist plus cancer therapy treatment include GHR, PRLR or both GHR and PRLR. Expression levels in a tumor biopsy are measured and quantified by performing a diagnostic test that measures levels of mRNA encoding these proteins that is expressed by the tumor cells. For example, the tumor biopsy sample could be processed to isolate mRNA which is then reverse transcribed into cDNA. The amount of cDNA derived from genes that encode these two receptors could then be measured using a variety of standard assays including qPCR analysis or gene chip analysis. Patients whose tumors express elevated levels of GHR, PRLR or both GHR and PRLR are potential candidates for receiving treatment with the disclosed combination therapy. Alternatively, the levels of these target proteins could be measured using techniques that directly measure the amount of these proteins present in the tumor. This approach includes the use of assays such as Western blots or ELISA assays.

Additional genes whose expression levels are key indicators of effective response to the disclosed hGHR antagonist plus cancer therapeutic combination therapy include a key set of ATP-binding cassette (ABC) drug efflux pumps; ABCB1, ABCB5, ABCB8, ABCC1, ABCC2, ABCG1 and ABCG2. As with the target receptors described above, elevated levels of expression of at least some of these proteins identifies patients for which the disclosed combination hGHR antagonist plus cancer therapeutic agent would be effective. The levels of expression of these key genes are determined using the analytical techniques described above on samples derived from patient biopsies.

In addition to the drug efflux pump proteins discussed herein, expression levels of a selected set of genes involved in promoting the adverse progression of cancer driven by the Epithelial to Mesenchymal Transition (EMT) can be measured. The set of key EMT modulators analyzed in a preliminary diagnostic analysis of a patient biopsy include CDH1, CDH2, SNAIL SNAI2, TGFB1, TGFB2, TGFB3, TGFBR2, TWIST1, TWIST2, VIM, ZEB1 and ZEB2. Elevated levels of expression of these genes further identify patients that are candidates for effective treatment with the disclosed combination GHR antagonist plus cancer therapeutic agent. The levels of expression of these genes would be determined by the analytical methods described above.

In addition to the target receptors GHR and PRLR, Insulin Like Growth Factor 1 (IGF-1), Insulin Like Growth Factor Binding Protein 3 (IGFBP3), suppressor of cytokine signaling (SOCS) -1, -2, -3, and cytokine inducible SH2 containing protein (CISH) are important genes whose (RNA or protein) expression levels in the tumor biopsy (all the above) or serum (IGF1 and IGFBP3) can be used to identify patients who will respond effectively to treatment with the disclosed GHR antagonist. As with the target receptor proteins, the levels of these GH inducible downstream signaling factors are determined by gene expression analysis using mRNA gene expression techniques or, preferably, serum protein quantification techniques. IGF-1, IGFBP3, SOCS-1, -2, -3 and CISH are particularly useful for identifying patients that would be effectively treated by continuing administration of the GHR antagonist following completion of a combination therapy using GHR antagonist plus cancer chemotherapeutic agent.

All literature and similar material cited in this application, including, but not limited to, patents, patent applications, articles, books, treatises, and web pages, regardless of the format of such literature and similar materials, are expressly incorporated by reference in their entirety. Should one or more of the incorporated references and similar materials differs from or contradicts this application, including but not limited to defined terms, term usage, described techniques, or the like, this application controls.

As previously stated and as used herein, the singular forms "a," "an," and "the," refer to both the singular as well as plural, unless the context clearly indicates otherwise. The term "comprising" as used herein is synonymous with "including," "containing," or "characterized by," and is inclusive or open-ended and does not exclude additional, unrecited elements or method steps. Although many methods and materials similar or equivalent to those described herein can be used, particular suitable methods and materials are described herein. Unless context indicates otherwise, the recitations of numerical ranges by endpoints include all numbers subsumed within that range. Furthermore, references to "one implementation" are not intended to be interpreted as excluding the existence of additional implementations that also incorporate the recited features. Moreover, unless explicitly stated to the contrary, implementations "comprising" or "having" an element or a plurality of elements having a particular property may include additional elements whether or not they have that property.

The terms "substantially" and "about" used throughout this specification are used to describe and account for small fluctuations, such as due to variations in processing. For example, these terms can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%, and/or 0%.

Underlined and/or italicized headings and subheadings are used for convenience only, do not limit the disclosed subject matter, and are not referred to in connection with the interpretation of the description of the disclosed subject matter. All structural and functional equivalents to the elements of the various implementations described throughout this disclosure that are known or later come to be known to those of ordinary skill in the art are expressly incorporated herein by reference and intended to be encompassed by the disclosed subject matter. Moreover, nothing disclosed herein is intended to be dedicated to the public regardless of whether such disclosure is explicitly recited in the above description.

There may be many alternate ways to implement the disclosed inventive subject matter. Various functions and elements described herein may be partitioned differently from those shown without departing from the scope of the disclosed inventive subject matter. Generic principles defined herein may be applied to other implementations. Different numbers of a given module or unit may be employed, a different type or types of a given module or unit may be employed, a given module or unit may be added, or a given module or unit may be omitted.

Regarding this disclosure, the term "a plurality of" refers to two or more than two. Unless otherwise clearly defined, orientation or positional relations indicated by terms such as "upper" and "lower" are based on the orientation or positional relations as shown in the figures, only for facilitating description of the present invention and simplifying the description, rather than indicating or implying that the referred devices or elements must be in a particular orientation or constructed or operated in the particular orientation, and therefore they should not be construed as limiting the present invention. The terms "connected", "mounted", "fixed", etc. should be understood in a broad sense. For example, "connected" may be a fixed connection, a detachable connection, or an integral connection; a direct connection, or an indirect connection through an intermediate medium. For an ordinary skilled in the art, the specific meaning of the above terms in the present invention may be understood according to specific circumstances.

It should be appreciated that all combinations of the foregoing concepts and additional concepts discussed in greater detail herein (provided such concepts are not mutually inconsistent) are contemplated as being part of the disclosed inventive subject matter. In particular, all combinations of claimed subject matter appearing at the end of this disclosure are contemplated as being part of the inventive subject matter disclosed herein. While the disclosed inventive subject matter has been illustrated by the description of example implementations, and while the example implementations have been described in certain detail, there is no intention to restrict or in any way limit the scope of the appended claims to such detail. Additional advantages and modifications will readily appear to those skilled in the art. Therefore, the disclosed inventive subject matter in its broader aspects is not limited to any of the specific details, representative devices and methods, and/or illustrative examples shown and described. Accordingly, departures may be made from such details without departing from the spirit or scope of the general inventive concept.

The following references form part of the specification of the present application and each reference is incorporated by reference herein, in its entirety, for all purposes.

1. Pasut, G. and Veronese, M. (2012) State of the Art in Pegylation: The Great Versatility Achieved After Forty Years of Research. *J. Controlled Release* 161, 461-472.
2. Parveen, S. and Sahoo, S. K. Nanomedicine: Clinical Applications of Polyethylene Glycol Conjugated to Proteins and Drugs *Clin. Pharmacokinet.* 45, 965-988.
3. Alconcel, S. N. S., Baas, A. S. and Maynard, H. D. (2011) FDA-Approved Poly(ethylene glycol)-Protein Conjugate Drugs. *Polymer Chemistry* 2, 1442-1448.
4. Kling, J. (2013) Pegylation of Biologics: A Multipurpose Solution. *Bioprocess International* 11, 35-43.
5. Perry, J. K., Wu, Z.-S., Mertani, H. C., Zhu, T., and Lobie, P. E. (2017) "Tumour-Derived Human Growth Hormone as a Therapeutic Target in Oncology" *Trends in Endocrinology and Metabolism* 28: 587-596.
6. Basu, R., Qian, Y., and Kopchick, J. J. (2018) "Lessons from growth hormone receptor gene-disrupted mice: are there benefits of endocrine defects?" *European Journal of Endocrinology* 178: R155-R181.
7. Coffin, V. (2017) "Prolactin Receptor Targeting in Breast and Prostate Cancers: New Insights into an Old Challenge" *Pharmacology and Therapeutics* 179: 111-126.
8. Sustarsic, E. G., Junnila, R. K., and Kopchick, J. J. (2013) "Human Metastatic Melanoma Cell Lines Express High Levels of Growth Hormone Receptor and Respond to GH Treatment" *Biochem Biophys Res Commun.* 441: 144-150.
9. Bukowski, K., Kciuk, M., and Kontek, R. (2020) "Mechanisms of Multidrug Resistance in Cancer Chemotherapy" *Int. J. Mol. Sci.* 21, 3233

10. Basu, R., and Kopchick, J. J. (2019) "The Effects of Growth Hormone on Therapy Resistance in Cancer" *Cancer Drug Resistance* 2: 827-846,
11. Wu, A. M. L., Dalvi, P., Lu, X., Yang, M., Riddick, D. S., et al. (2013) "Induction of multidrug resistance transporter ABCG2 by prolactin in human breast cancer cells" *Molecular Pharmacology* 83:377-88.
12. Neradugomma, N. K., Subramaniam, D., Tawfik, O. W., Coffin, V., Kumar, T. R., et al. (2014) "Prolactin signaling enhances colon cancer stemness by modulating Notch signaling in a Jak2-STAT3/ERK manner" *Carcinogenesis* 35:795-806
13. Zatelli, M. C., Minoia, M., Mole, D., Cason, V., Tagliati, F., Margutti, A., Bondanelli, M., Ambrosio, M. R., and Uberti, E.d (2009) "Growth Hormone Excess Promotes Breast Cancer Chemoresistance" *Journal of Clinical Endocrinology and Metabolism* 94: 3931-3938.
14. Minoia, M., Gentilin, E., Mole, D., Rossi, M., Filieri, C., Tagliati, F., Baroni, A., Ambrosio, M. R., and Uberti, E.d, Zatelli, M. C. "Growth Hormone Receptor Blockade Inhibits Growth Hormone-Induced Chemoresistance by Restoring Cytotoxic-Induced Apoptosis in Breast Cancer Cells Independently of Estrogen Receptor Expression" *Journal of Clinical Endocrinology and Metabolism* 97: E907-E916.

What is claimed:

1. A composition for treating a disease or condition responsive to human growth hormone receptor antagonists, comprising:
   (a) a modified human growth hormone receptor antagonist, wherein the human growth hormone receptor antagonist comprises:
      (i) human growth hormone receptor antagonist G120K, wherein two amino acids of human growth hormone receptor antagonist G120K have been changed to cysteine, wherein the two amino acids changed to cysteine are T142 and H151, and wherein the human growth hormone receptor antagonist G120K-H151C-T142-C has a DNA sequence of SEQ ID NO: 3, and an amino acid sequence of SEQ ID NO: 4; and
      (ii) polyethylene glycol molecule conjugated to each substituted cysteine in the human growth hormone receptor antagonist G120K-H151C-T142C, wherein the polyethylene glycol molecules conjugated to the two amino acids changed to cysteine are two 4.5 kDa branched polyethylene glycols each containing three carboxylate anions; and
   (b) an anti-cancer composition.

2. The composition of claim 1, wherein the disease or condition responsive to human growth hormone receptor antagonists is a cancer that expresses predetermined levels of growth hormone receptor (GHR); predetermined levels of prolactin receptor (PRLR); predetermined levels of both GHR and PRLR; predetermined levels of ATP-binding cassette (ABC)-transporters; or predetermined levels of epithelial to mesenchymal transition (EMT) mediators.

3. The composition of claim 1, wherein the disease or condition responsive to human growth hormone receptor antagonists is cancer, and wherein the cancer is breast cancer, central nervous system cancer, melanoma, non-small cell lung cancer, ovarian cancer, prostate cancer, renal cancer, pancreatic cancer, endometrial cancer, meningioma, colorectal cancer, colon cancer, neuroblastoma, stomach cancer, liver cancer, lymphoma, combinations thereof, or any other cancer expressing predetermined amounts of GHR, PRLR, ABC transporters, EMT mediators, or combinations thereof.

4. The composition of claim 1, wherein the following amino acid substitutions have been further made in SEQ ID NO: 4: H18D, H21N, R167N, K168A, D171S, K172R, E174S, and I179T, and wherein these mutations are operative to prevent binding to a prolactin receptor.

5. The composition of claim 1, wherein the polyethylene glycol molecule contains a maleimide group for conjugation to a free sulfhydryl group.

6. The composition of claim 1, wherein the anti-cancer composition is an antimetabolite.

7. The composition of claim 6, wherein the antimetabolite is gemcitabine.

8. The composition of claim 1, wherein the polyethylene glycol molecule is prepared by stepwise organic chemistry and is a substantially pure single compound.

* * * * *

SEQUENCE LISTING

<160> NUMBER OF SEQ ID NOS: 4

<210> SEQ ID NO 1
<211> LENGTH: 567
<212> TYPE: DNA
<213> ORGANISM: Artificial Sequence
<220> FEATURE:
<223> OTHER INFORMATION: G120K (DNA) Human Growth Hormone Antagonist G120K

<400> SEQUENCE: 1

```
ttcccaacca ttcccttatc caggcttttt gacaacgcta tgctccgcgc catcgtctgc      60
accagctggc ctttgacacc taccaggagt ttgaagaagc ctatatccca aggaacagaa     120
gtattcattc ctgcagaacc cccagacctc cctctgtttc tcagagtcat tccgacaccc     180
tccaacaggg aggaaacaca acagaaatcc aacctagagc tgctccgatc tccctgctgc     240
tcatccagtc gtggctggag cccgtgcagt tcctcaggag tgtcttgcca acagcctggt     300
gtacggcgcc tctgacagca acgtctatga cctcctaaag gacctgagga aaagatccaa     360
acgctgatgg ggaggctgga agatggcagc ccccggactg ggcaatcttc aagcagacct     420
acagcaagtt cgacacaaac tcacacaacg atgacgcact actaagaact acgggctgct     480
ctactgcttc aggaaggaca tggacaaggt cgagacattc ctcgcatcgt gcagtgccgc     540
tctgtggagg gcagctgtgg cttctag                                        567
```

<210> SEQ ID NO 2
<211> LENGTH: 188
<212> TYPE: PRT
<213> ORGANISM: Artificial Sequence
<220> FEATURE:
<223> OTHER INFORMATION: G120K (amino acid) Human Growth Hormone Antagonist G120K (Mature Form)

<400> SEQUENCE: 2

```
Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Leu Cys Phe Ser Glu Ser Ile Pro Thr Pro Ser Asn Arg Glu
    50                  55                  60

Glu Thr Gln Gln Lys Ser Asn Leu Glu Leu Leu Arg Ile Ser Leu Leu
65                  70                  75                  80

Leu Ile Gln Ser Trp Leu Glu Pro Val Gln Phe Leu Arg Ser Val Phe
                85                  90                  95
```

```
Ala Asn Ser Leu Val Tyr Gly Ala Ser Asp Ser Asn Val Asp Leu Leu
            100                 105                 110

Lys Asp Leu Glu Glu Lys Ile Gln Thr Leu Met Gly Arg Leu Glu Asp
        115                 120                 125

Gly Ser Pro Arg Thr Gly Gln Ile Phe Lys Gln Thr Tyr Ser Lys Phe
    130                 135                 140

Asp Thr Asn Ser His Asn Asp Asp Ala Leu Leu Lys Asn Tyr Gly Leu
145                 150                 155                 160

Leu Tyr Cys Phe Arg Lys Asp Met Lys Val Glu Thr Phe Leu Arg Ile
                165                 170                 175

Val Gln Cys Arg Ser Val Glu Gly Ser Cys Gly Phe
            180                 185
```

<210> SEQ ID NO 3
<211> LENGTH: 576
<212> TYPE: DNA
<213> ORGANISM: Artificial Sequence
<220> FEATURE:
<223> OTHER INFORMATION: G120K-H151C-T142C-dPEGA2 (DNA) Synthetic
      Constructs / Mutant Human Growth Hormone Antagonists

<400> SEQUENCE: 3

```
ttcccaacca ttcccttatc caggcttttt gacaacgcta tgctccgcgc ccatcgtctg     60
caccagctgg cctttgacac ctaccaggag tttgaagaag cctatatccc aaaggaacag    120
aagtattcat tcctgcagaa cccccagacc tccctctgtt tctcagagtc tattccgaca    180
ccctccaaca gggaggaaac acaacagaaa tccaacctag agctgctccg catctccctg    240
ctgctcatcc agtcgtggct ggagcccgtg cagttcctca ggagtgtctt cgccaacagc    300
ctggtgtacg gcgcctctga cagcaacgtc tatgacctcc taaaggacct agaggaaaag    360
atccaaacgc tgatggggag gctggaagat ggcagccccc ggactgggca gatcttcaag    420
cagtgctaca gcaagttcga cacaaactca tgcaacgatg acgcactact caagaactac    480
gggctgctct actgcttcag gaaggacatg gacaaggtcg agacattcct gcgcatcgtg    540
cagtgccgct ctgtggaggg cagctgtggc ttctag                              576
```

<210> SEQ ID NO 4
<211> LENGTH: 191
<212> TYPE: PRT
<213> ORGANISM: Artificial Sequence
<220> FEATURE:
<223> OTHER INFORMATION: G120K-H151C-T142C-dPEGA2 (amino acid)
      Synthetic Constructs / Mutant Human Growth Hormone Antagonists

<400> SEQUENCE: 4

```
Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
```

-continued

```
                100                 105                 110
Leu Leu Lys Asp Leu Glu Glu Lys Ile Gln Thr Leu Met Gly Arg Leu
        115                 120                 125

Glu Asp Gly Ser Pro Arg Thr Gly Gln Ile Phe Lys Gln Cys Tyr Ser
        130                 135                 140

Lys Phe Asp Thr Asn Ser Cys Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
                180                 185                 190
```